(12) United States Patent
Konya

(10) Patent No.: US 9,662,046 B2
(45) Date of Patent: May 30, 2017

(54) LANCING ACTUATOR

(71) Applicant: Roche Diabetes Care, Inc., Indianapolis, IN (US)

(72) Inventor: Ahmet Konya, Ludwigshafen (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 195 days.

(21) Appl. No.: 14/325,471

(22) Filed: Jul. 8, 2014

(65) Prior Publication Data
US 2015/0012027 A1  Jan. 8, 2015

(30) Foreign Application Priority Data
Jul. 8, 2013  (EP) ..................................... 13175514

(51) Int. Cl.
*A61B 17/14* (2006.01)
*A61B 5/15* (2006.01)
(Continued)

(52) U.S. Cl.
CPC .......... *A61B 5/1411* (2013.01); *A61B 5/1519* (2013.01); *A61B 5/150022* (2013.01);
(Continued)

(58) Field of Classification Search
CPC  A61B 5/14; A61B 5/1411; A61B 5/15; A61B 5/150412; A61B 5/150435;
(Continued)

(56) References Cited

U.S. PATENT DOCUMENTS 6,419,661  B1  7/2002  Kuhr et al.
2002/0169470  A1  11/2002  Kuhr et al.
(Continued)

FOREIGN PATENT DOCUMENTS

CN  1968650  A  5/2007
CN  1968652  A  5/2007
(Continued)

*Primary Examiner* — Robert Lynch
(74) *Attorney, Agent, or Firm* — Bose McKinney & Evans LLP

(57) ABSTRACT

A lancing actuator (114) includes a drive element (118) for driving a lancing element, the drive element being guided within a housing (112), a combined compression and torsion element (120) which, by a relaxing movement thereof, is adapted to drive the lancing motion, a combined triggering and driving device (122) having an actuating element (124) and a locking device (126), wherein the actuating element has an initial state and an actuated state and is accessible from the outside of the housing, wherein, in the initial state, the drive element is locked in the locking device under a torsional stress exerted by the combined compression and torsion element, wherein the combined triggering and driving device is configured in a manner that, when the actuating element makes a movement along an actuation path from the initial state into the actuated state, a torque is exerted on the drive element which prevails over the torsional stress exerted by the combined compression and torsion element such that the drive element is released from the locking device, which results in a triggering of the lancing motion.

26 Claims, 13 Drawing Sheets

(51) Int. Cl.
*A61B 5/145* (2006.01)
*A61B 5/151* (2006.01)

(52) U.S. Cl.
CPC ....... *A61B 5/15111* (2013.01); *A61B 5/15117* (2013.01); *A61B 5/15128* (2013.01); *A61B 5/15194* (2013.01); *A61B 5/150412* (2013.01); *A61B 5/150503* (2013.01); *A61B 5/14* (2013.01); *A61B 5/15* (2013.01); *A61B 5/151* (2013.01); *A61B 5/15146* (2013.01); *A61B 5/150435* (2013.01); *A61B 5/150519* (2013.01)

(58) Field of Classification Search
CPC ........ A61B 5/150503; A61B 5/150511; A61B 5/150519; A61B 5/151; A61B 5/15107; A61B 5/15111; A61B 5/15113; A61B 5/15117; A61B 5/15128; A61B 5/15146; A61B 5/1519

See application file for complete search history.

(56) References Cited

U.S. PATENT DOCUMENTS

| | | | |
|---|---|---|---|
| 2003/0216767 A1* | 11/2003 | List | A61B 5/1411 606/181 |
| 2004/0260326 A1 | 12/2004 | Lipoma et al. | |
| 2012/0053561 A1* | 3/2012 | Simonton | A61M 37/0069 604/506 |
| 2013/0085517 A1* | 4/2013 | Keil | A61B 5/1411 606/182 |

FOREIGN PATENT DOCUMENTS

| | | |
|---|---|---|
| EP | 0885590 B1 | 1/2008 |
| EP | 1810615 B1 | 9/2008 |
| JP | 2003339679 A | 12/2003 |
| WO | 2006027101 A1 | 3/2006 |
| WO | WO2008130259A1 A1 | 10/2008 |
| WO | 2009046957 A3 | 4/2009 |
| WO | 2011134639 A1 | 11/2011 |

* cited by examiner

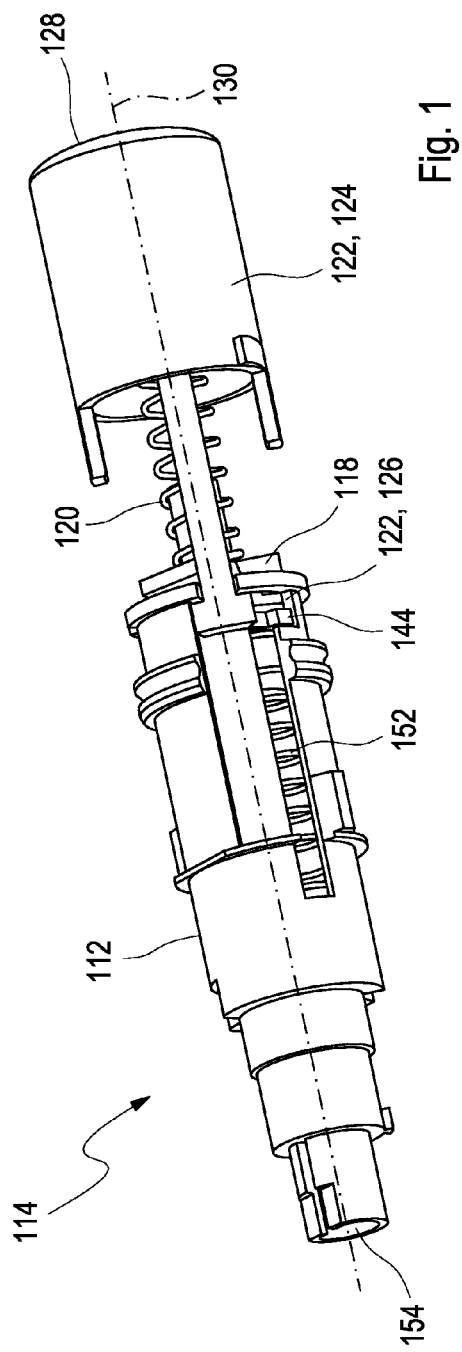
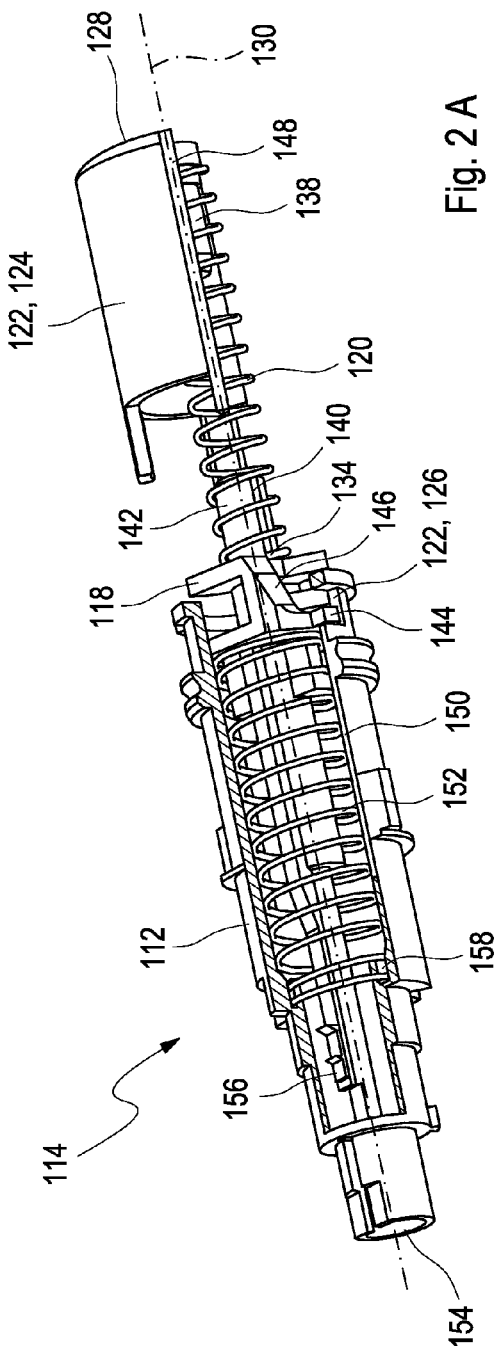

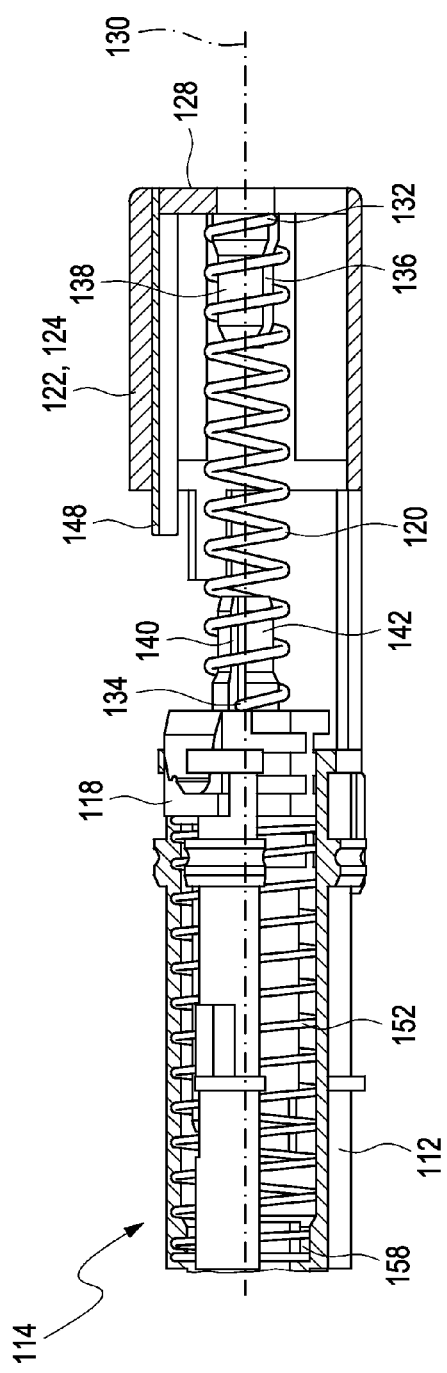
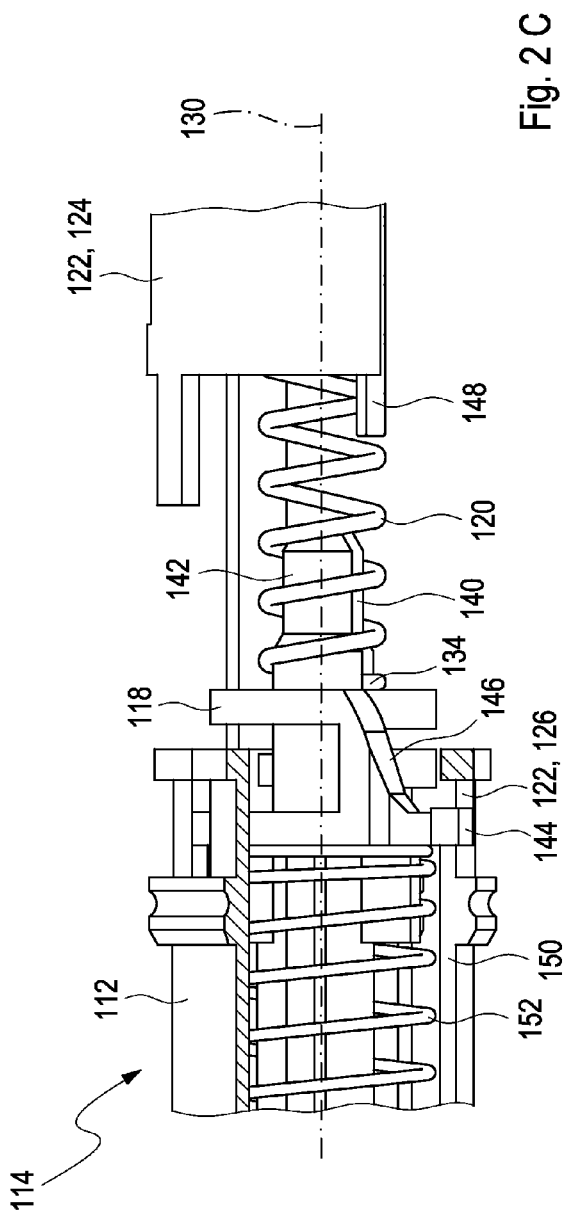
Fig. 2 B
Fig. 2 C

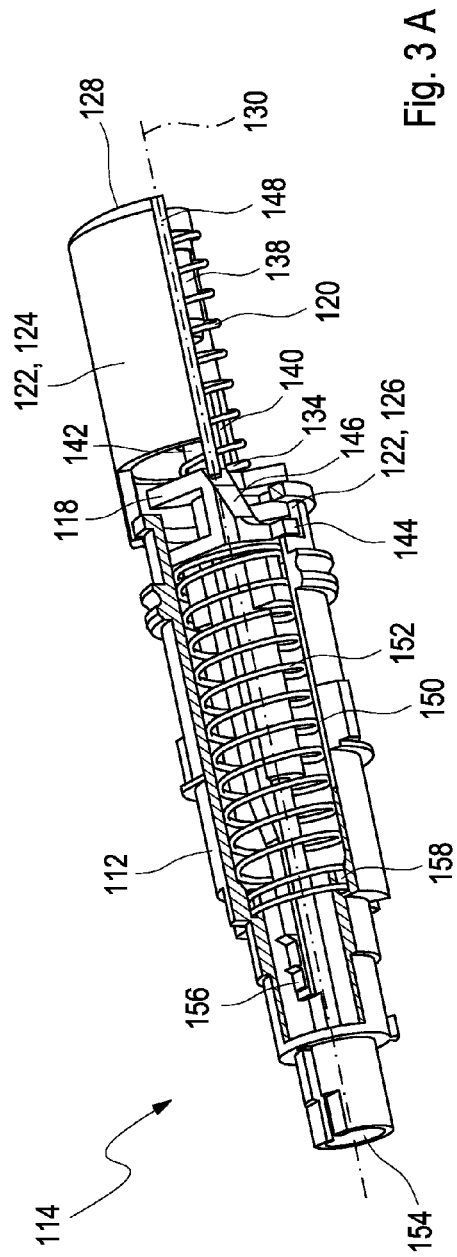
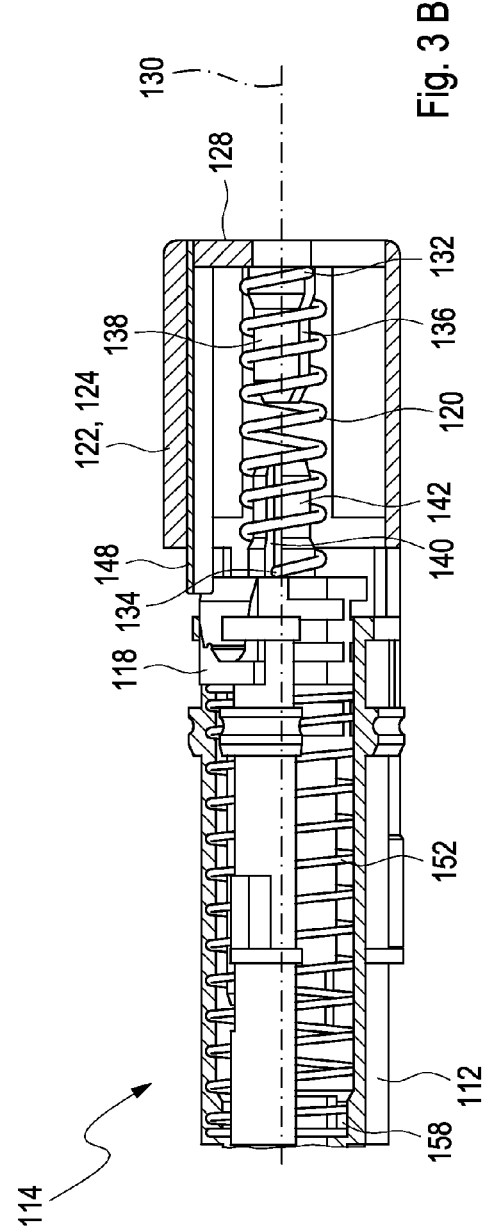

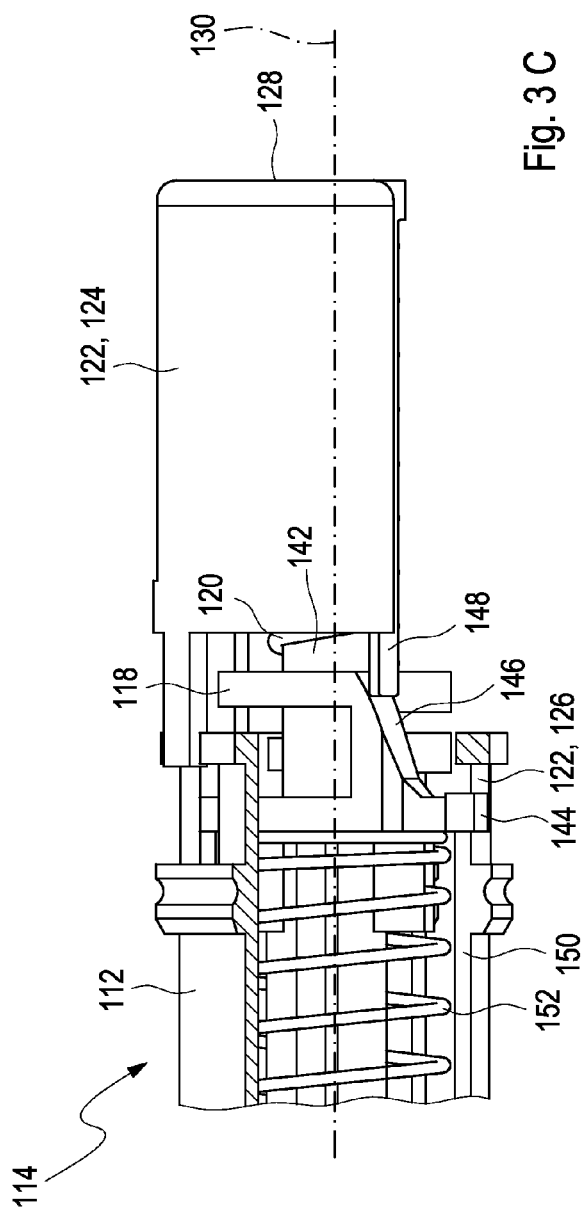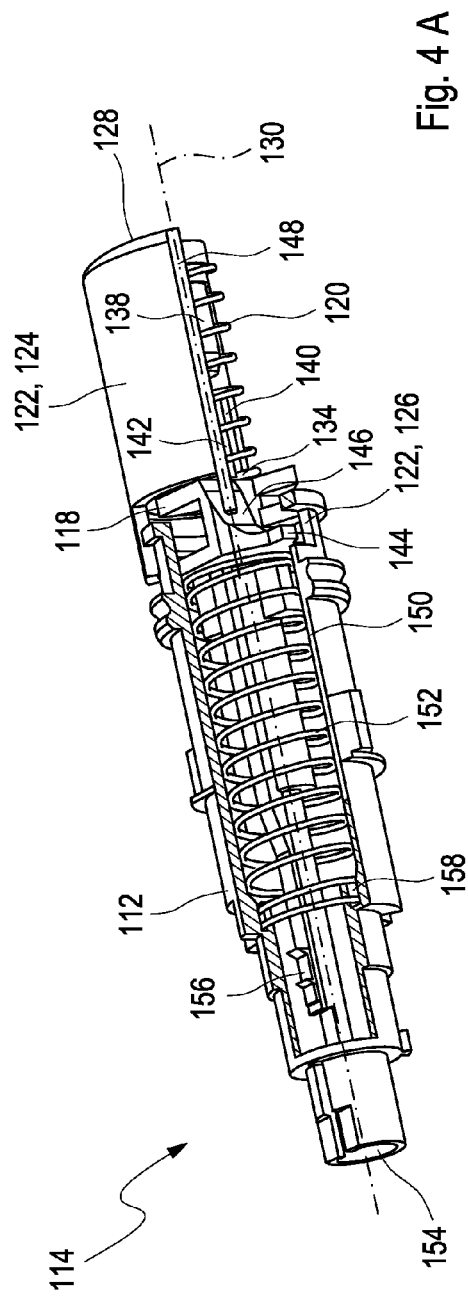

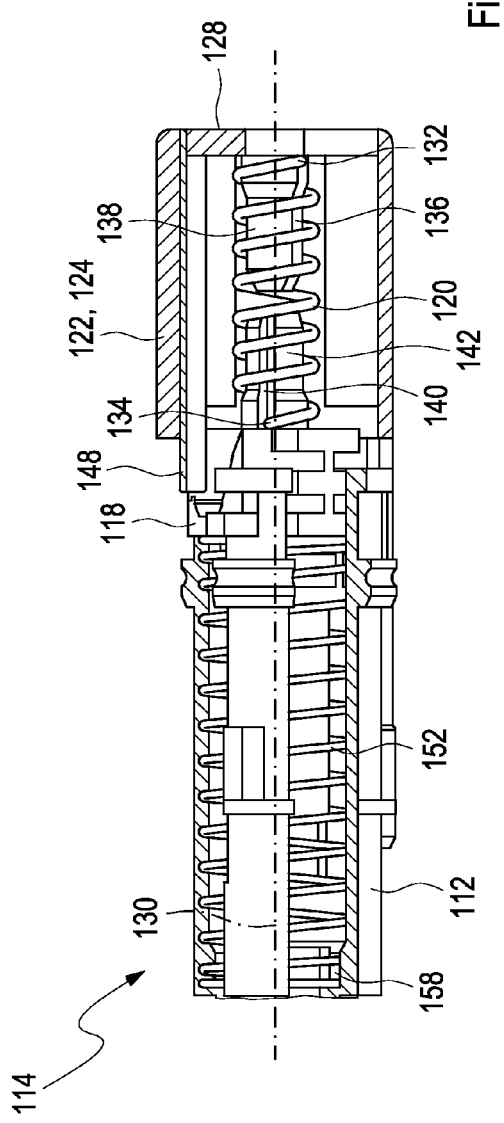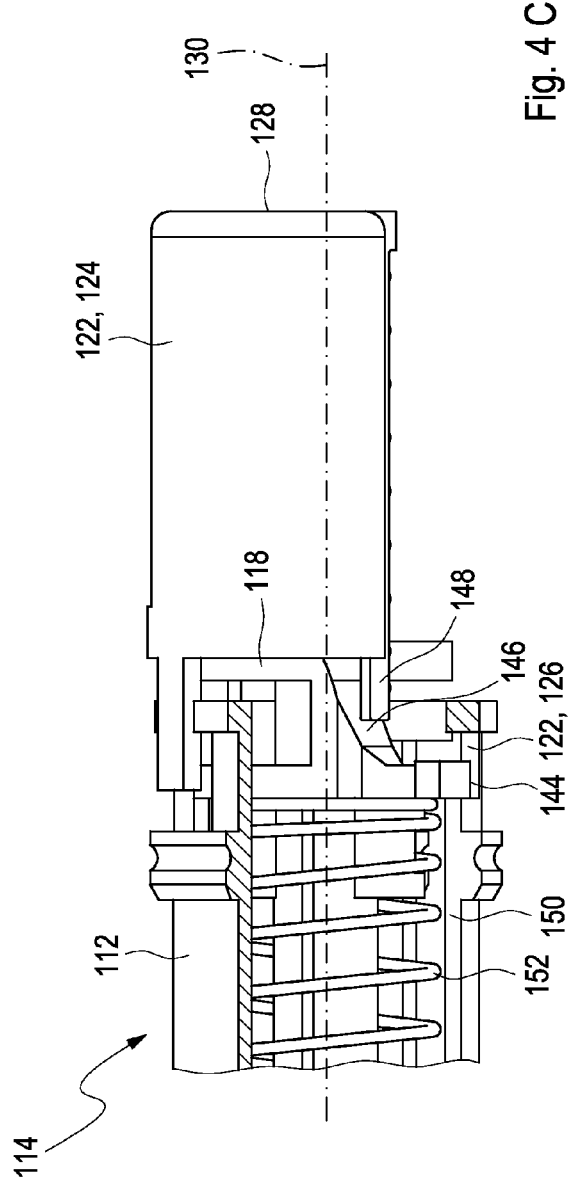

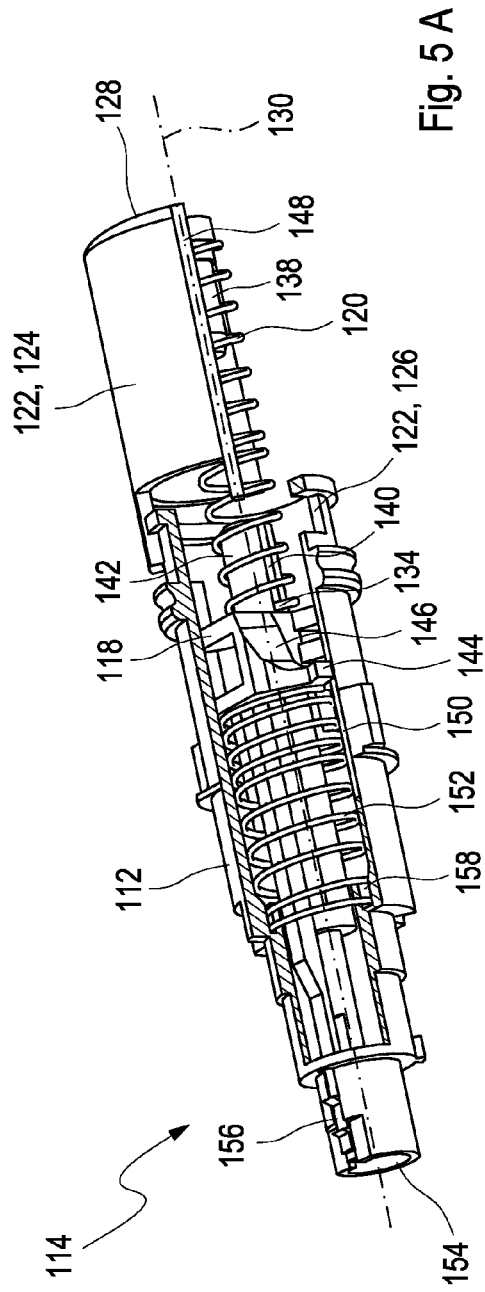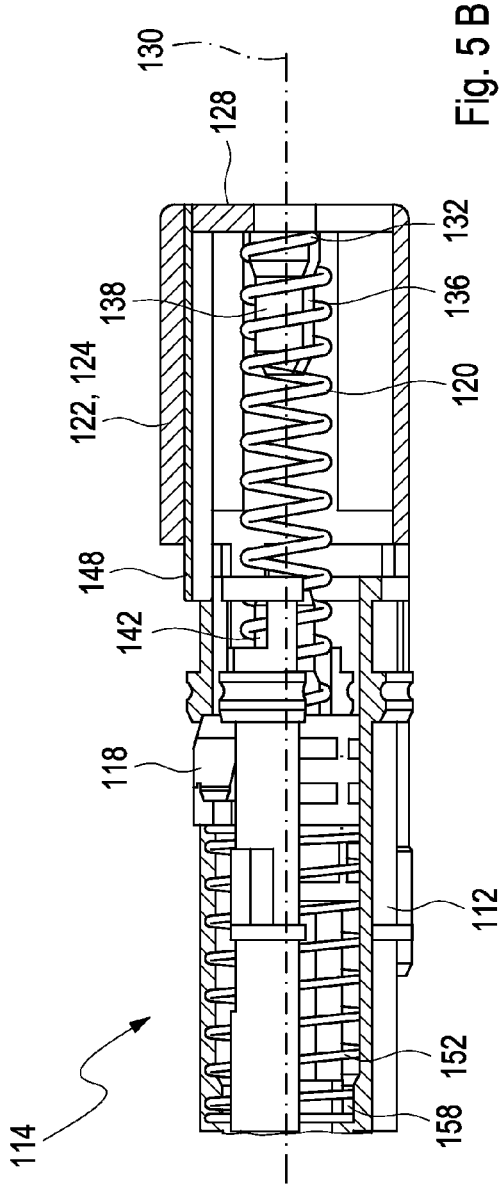

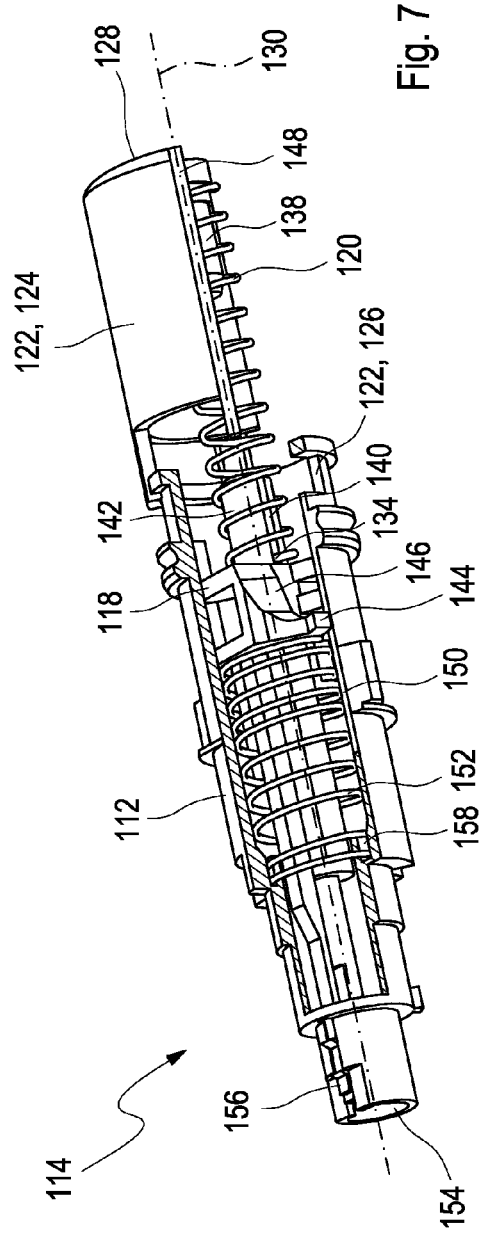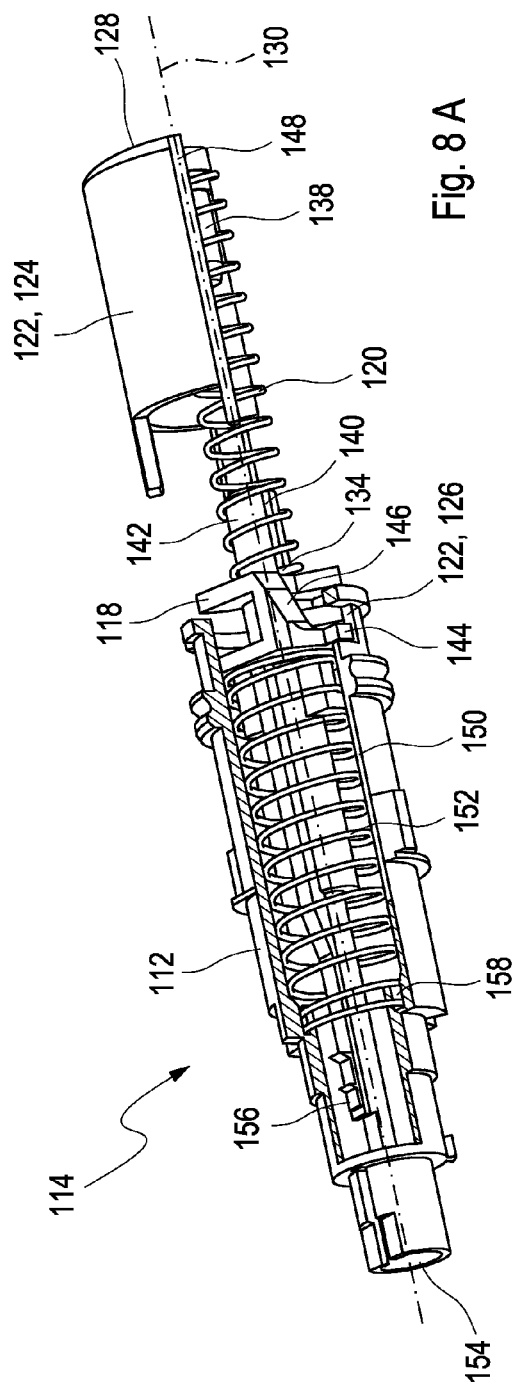

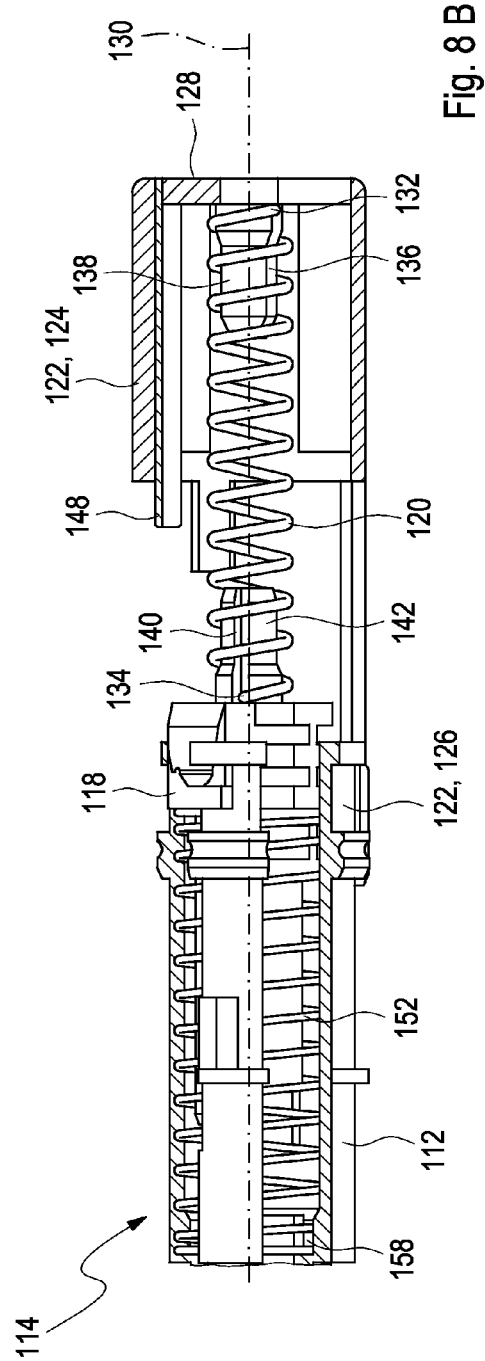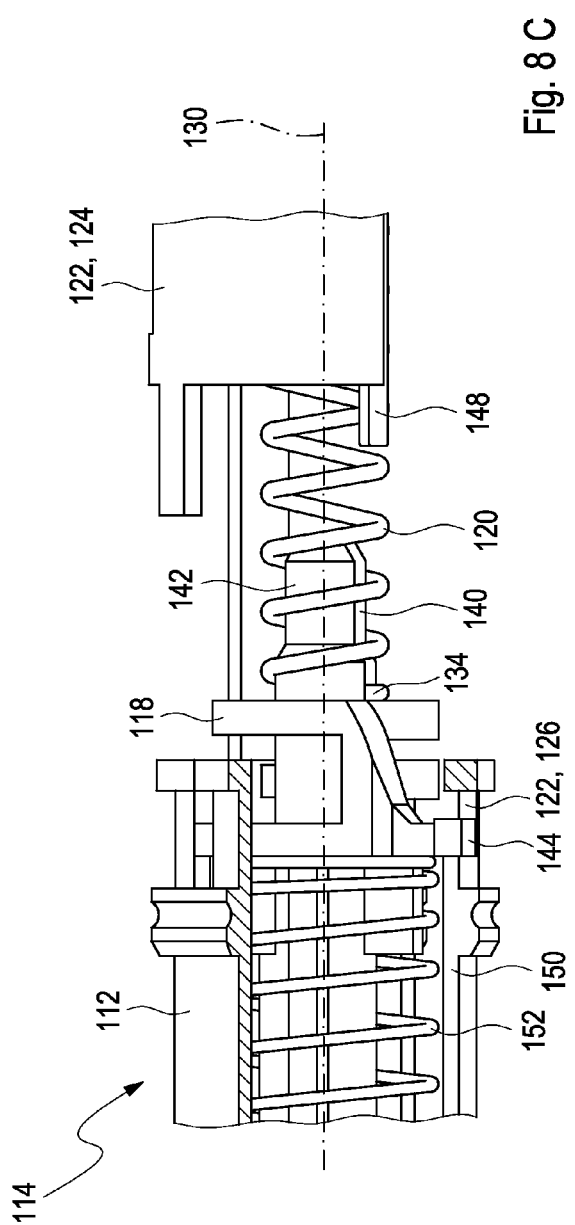

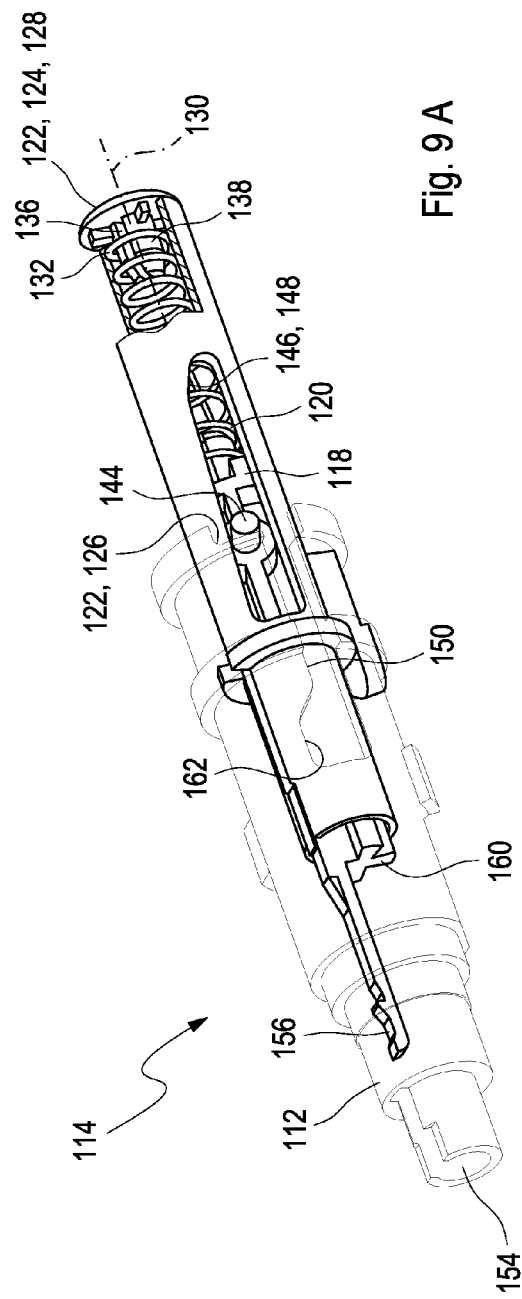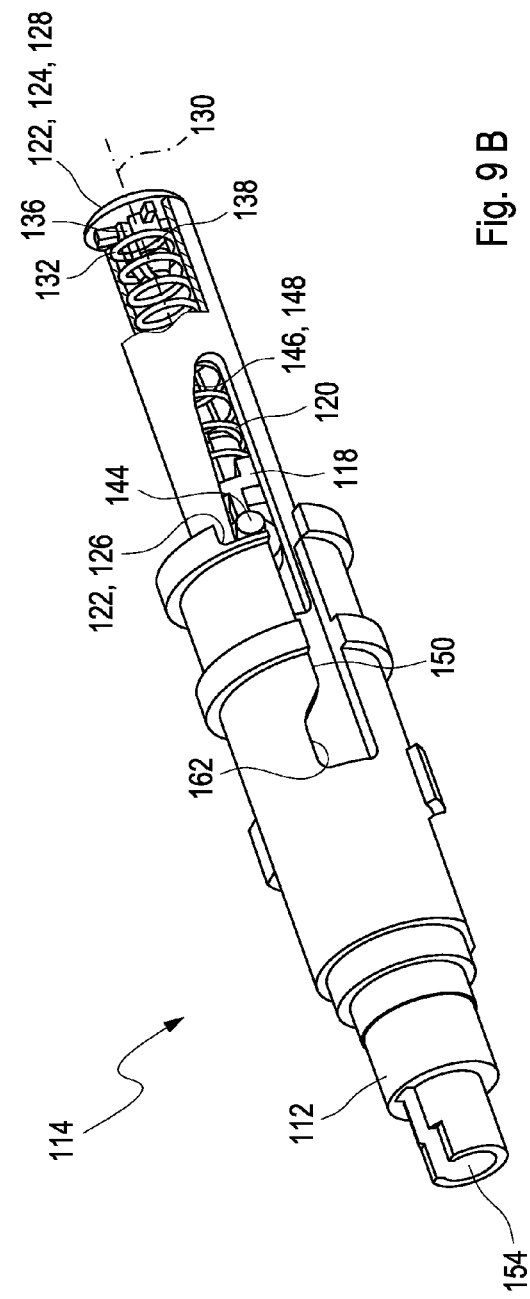

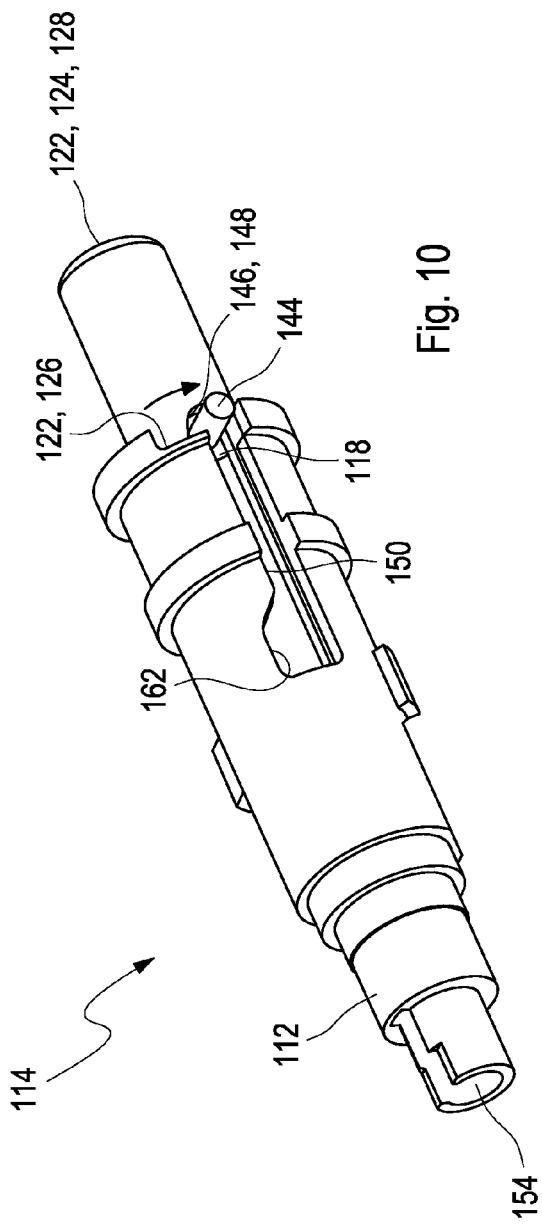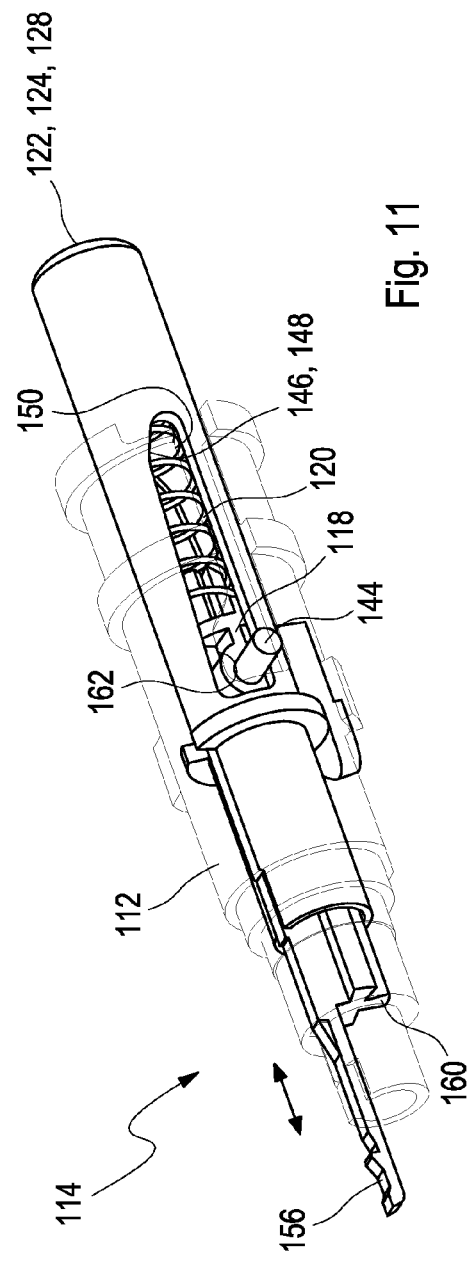

LANCING ACTUATOR

FIELD OF THE INVENTION

The invention relates to a lancing actuator for driving a lancing element which is configured for sampling a body fluid. The invention further relates to a lancing device, comprising the lancing actuator and at least one lancing element, which is adapted for perforating a skin portion of a user during a puncture process. The invention further relates to a method for performing a lancing motion by operating the lancing actuator. The lancing actuator, the lancing device, and the method of the present invention may optionally be used in the field of determining the presence and/or the concentration of one or more analytes in a body fluid such as blood, interstitial fluid or other types of body fluids. As an example, the at least one analyte may be one or more of glucose, cholesterol, lactate and triglyceride. Additionally or alternatively, however, other types of analytes may be determined. The invention may be applied, particularly for medical purposes, both in the field of home monitoring and in the field of professional diagnostics such as in hospitals and/or intensive care institutions. In the following, without intending to restrict the scope of the present invention and without restricting the application of the invention in other fields, the invention will be mainly disclosed in the context of determining a concentration of glucose in blood and/or interstitial fluid.

RELATED ART

In the art of medical diagnostics, it is frequently required to analyze one or more samples of a body fluid, particularly of blood and/or of an interstitial fluid, for the purpose of monitoring an analyte which is present in the body fluid. In order to generate and, optionally, analyze a sample of a body fluid, a large number of lancing devices are known, for both professional care and home monitoring. In order to perform a frequent number of measurements, particularly in regularly determining the glucose concentration in the blood of a user, it is required to remove or at least reduce the implications of any obstacle which might impede the use of the lancing device by the user as far as possible. Within this regard, a reduction of the apparent size of the lancing device could facilitate its application to at least some extent.

U.S. Pat. No. 3,030,959 A discloses a pencil-shaped lancing device which comprises a cylindrical housing wherein a central tube is located which is advanced by a first spring. Further located within the housing is a second spring which serves as a return spring for the first spring. Arranged in the central tube for a longitudinal displacement is a further tube which is actuated by a feeding spring, which, upon activating a pull knob permanently connected to the central tube, is tensioned and produces a force upon the further tube which acts upon a spring collet which holds a puncturing needle.

U.S. Pat. No. 4,203,446 A describes a lancing device which comprises means for preventing a recoil of a lancet holder which include a mass which is mounted for a motion within the housing in opposite to a motion of the lancing element, wherein an impact spring is provided between the mass and the housing in order to resist a motion between the mass and the housing. Additionally, a striker spring may be mounted at one end of the mass.

DE 100 22 720 A1 exhibits a lancing device which comprises a drive element adapted for driving the lancing element to perform a lancing motion, the drive element being guided within a housing, and a magazine comprising a plurality of lancing elements which may be successively coupled to a lancet holder. Further, a return spring is provided which is configured to return the magazine in its initial position after each lancing motion and to turn the drive element by means of a gear into a position which allows coupling the next lancing element onto the lancing holder.

US 2003/0199892 A1 discloses a lancing device comprising a lancet holder which holds a lancing element and a drive element at the end of the lancet holder. When the lancing element moves forward to pierce a portion of a skin of a user, a return elastic member is contracted, accumulates elasticity and then bounces backwards, by which motion the lancing element pierces the skin and is then retracted. In a specific embodiment, the drive element includes a hollow and cylindrical pushing member, wherein an impact-transmitting member and a first elastic member are inserted into the hollow pushing member, wherein the first elastic member gives elasticity to the impact-transmitting member. A second elastic member is arranged additionally around the circumference of the pushing member in order to return the pushing member after a pushing force has been removed.

US 2008/0195132 A1 describes a lancing device comprising a drive element which is movably mounted within a housing and which is configured to receive a lancing element at its front end, a first, typically helical spring adapted to move the drive element between an initial state and an actuated state, and a second, typically helical spring adapted to move the drive element between an initial state and an intermediate state. In particular, an axial expansion of the first spring causes an axial compression of the second spring, whereby the second spring is typically sized to resist greater compression forces than the first spring and particularly biases a rear push-button.

DE 10 2009 055 874 A1 and DE 10 2010 004 370 A1 disclose lancing devices each comprising a lancet holder with a notch wherein a tension spring is inserted which has an end mounted to the housing. A tensioning and a subsequent relaxation of the tension spring move the lancet holder to perform a puncture process.

WO 2011/134639 A1 discloses a lancing device comprising a drive element adapted for driving a lancing element to perform a lancing motion, the drive element being guided within a housing, an elastic drive element which can be converted by tensioning from an untensioned into a tensioned state, which, after a triggering, is adapted to drive the lancing element, a combined tensioning and triggering device having an actuating element and a locking device, wherein the actuating element has an initial state and an actuated state and is accessible from the outside of the housing, wherein the drive element is first tensioned and then released when the actuating element is moved along an actuation path, whereby a release of the drive element is enabled when a certain point of the actuation path is reached.

It is therefore an objective to provide a lancing device, which comprises a lancing actuator and at least one lancing element, which at least partially overcomes any problems and/or shortcomings of lancing devices known according to the state of the art.

It is a particular objective to provide a lancing device, which comprises a lancing actuator and at least one lancing element, wherein the size of the lancing device is reduced with respect to the length of lancing devices known according to the state of the art.

It is a particular objective to achieve a reduction of the size of the lancing device in a manner that the lancing element is unaffected by the reduction as far as it is possible.

It is a particular objective to achieve the reduction of the size of the lancing device in a manner that the direct release function of the lancing element is, as far as possible, unaffected by the reduction.

It is a particular objective to achieve the reduction of the size of the lancing device in a manner that the depth of a puncture in a skin portion of a user is kept effectively constant over time without or with only little compensation.

It is a further objective to provide a lancing actuator which is adapted for driving the lancing element within the lancing device with reduced length.

It is a further objective to provide a method which is adapted for performing a lancing motion in the lancing device with reduced length by operating the lancing actuator adapted hereto.

It is a further objective to provide a method which is adapted for generating a sample of a body fluid by using the lancing device with reduced length.

SUMMARY

This problem is solved, with respect to a first aspect, by a lancing actuator for driving a lancing element which is configured to sample a body fluid, with respect to a second aspect, by a lancing device comprising the lancing actuator and at least one lancing element which is adapted for perforating a skin portion of a user during a puncture process, and, with respect to a third aspect, by a method for performing a lancing motion by operating the lancing actuator, with respect to each aspect, with the features of the independent claims. Optional embodiments, which might be realized in an isolated fashion or in any arbitrary combination, are listed in the dependent claims.

As used in the following, the terms "have", "comprise" or "include" or any arbitrary variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically", "typically", "more typically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a lancing actuator for driving a lancing element for sampling a body fluid is disclosed. As further used herein, a body fluid generally refers to an arbitrary body fluid of a human user or of an animal which may be generated by puncturing a skin portion of the human user or of the animal. In the following, typically, reference will be made to whole blood and/or interstitial fluid sampled from a human user. Still, other body fluids are generally feasible.

As further used herein, the lancing actuator is a device which is adapted, typically upon a triggering initiated by a user of the lancing device in which the lancing actuator is arranged, to evoke a lancing motion, which may be performed either through a direct impact on the lancing element by the lancing actuator or a part thereof or, more generally, via one or more additional elements, which may receive an impact from the lancing actuator or a part thereof and may forward the impact to the lancing element. Hereby, it is a preferable purpose of the lancing motion to move the lancing element in a manner that it may be able to perforate a skin portion of a user, such as by lancing, pricking or cutting, in order to sample a body fluid.

The lancing actuator comprises at least one drive element. As further used herein, the drive element is an arbitrary element arranged within the lancing actuator which provides the impact on the lancing element in order to perform the lancing motion, typically, either through a direct impact on the lancing element by the drive element or a part thereof or, more generally, via one or more additional elements, which may receive an impact from the drive element or a part thereof and may forward the impact to the lancing element. In order to be able to reliably perform the impact, the drive element is guided within at least one housing which encloses the lancing actuator. Hereby, the housing may partially or completely enclose the lancing actuator, including the drive element. Alternatively, the housing may directly cover the drive element only, either partially or completely, by which it may leave room for a second housing which is configured as a full or a partial enclosure for the lancing actuator.

As used herein, the housing is an arbitrary element which preferentially provides protection against mechanical influences from the outside, in particular protection against mechanical shocks. Thus, the housing may provide a full or partial enclosure against the surrounding environment. Further, the housing may provide protection against chemical influences, e.g. against moisture of the air which surrounds the lancing device. The housing typically is at least partially made as a rigid housing, i.e. a housing which is not visibly deformed by forces usually occurring during a use of the lancing device. As an example, the housing may fully or partially be made of a plastic material, e.g. of one or more thermoplastic materials.

According to a typical embodiment, the drive element may be guided within the housing by means of a control track and a control cam. As used herein, the control track is an arbitrary path along which the control cam may make a relative movement during at least a part of the movement of the drive element. Hereby, the control cam may be fastened to the drive element and/or may form an integral part of the drive element from where it may protrude in manner that it is able to engage into suitably formed structures, e.g. edges and/or recesses of the housing which are configured to suit for this purpose. In particular, the edges and/or recesses of the housing into which the control cam typically engages may form a guide curve suitable as the control track.

The lancing actuator further comprises a combined compression and torsion element. As used herein, the combined compression and torsion element is an arbitrary element which is accomplished to undergo the following kinds of motions:

a compression, i.e. an inward motion due to tension forces which push the element along its longitudinal axis, directed to decrease the size of the element in a longitudinal direction, i.e. the length of the element;

a relaxation, i.e. an outward motion due to a release of the element along its longitudinal axis after an application of the tension forces, directed to resume the length of the element prior to the application of the tension forces, whereby usually an overshooting with respect to the length of the element is initiated; and, a torsion, i.e. a twisting motion due to the application of a torque, i.e. forces which tend to rotate the element about its longitudinal axis.

The combined compression and torsion element typically comprises one or more springs, which may be formed of a wire of any diameter, e.g. a round, a square or a flat wire, as well as from a strip, made of a solid but flexible material, e.g. of annealed and hardened steel, or of a plastic material, including one or more thermoplastic materials. In particular, at least one helical spring is typically suited for this purpose. The combined compression and torsion element may comprise a first end and a second end, wherein each end is typically configured as a respective leg which points vertically in relation to the longitudinal axis. This kind of constitution allows the combined compression and torsion element to store and generate a torque about the longitudinal axis simply by a twisting motion of the first leg with relation to the second leg.

A particular purpose of the combined compression and torsion element is that it is adapted to drive the lancing motion by a relaxing movement of the combined compression and torsion element, whereby the relaxing movement may be in full, including an overshooting, or only partially. A partial relaxation may be achieved for example by integrating a return spring into the lancing actuator, whereby the return spring may be designed to counteract the movement of the combined compression and torsion element. However, in order to achieve a relaxation, the compression of the combined compression and torsion element is required prior to the relaxation. According to the present invention, the compression of the combined compression and torsion element is performed by means of an actuating element which will be described later.

The lancing actuator further comprises a combined triggering and driving device which includes the actuating element and a locking device. As used herein, the actuating element is an arbitrary element which comprises an initial state and an actuated state and is adapted to make a movement along an actuation path from the initial state into the actuated state, which may be achieved after a triggering of the actuating element. Particularly in order to achieve the triggering, the actuating element is accessible from the outside of the housing and, therefore, typically includes an operating button for the triggering the actuating element, particularly by a user of the lancing device. For this purpose, an operating button is typically mounted in a manner that it faces away from the lancing element. This requirement may be fulfilled by mounting the operating button at a rear end of the housing.

In the initial state, the drive element is locked in the locking device under a torsional stress which is exerted by the combined compression and torsion element. As used herein, the locking device is a single arbitrary element or, more generally, a combination of cooperating arbitrary elements which comprise means configured to keep an object in its current position. An example for such an element are suitably formed structures, e.g. edges and/or recesses of the housing, which are adapted to inhibit a movement of the control cam or of a sliding element described later, by which means the drive element is kept in position.

In a typical embodiment, the combined compression and torsion element is mounted to the lancing actuator comprising a torsional pretension. The torsional pretension safeguards that the drive element is firmly locked into the locking device, even under rough circumstances which may include vibration, shaking, etc.

Typically after the triggering of the actuating element, the actuating element makes a movement along the actuation path which leads the actuating element from the initial state into the actuated state. When the actuating element makes a movement along the actuation path from the initial state into the actuated state, a torque, i.e. forces which tend to rotate the drive element along a longitudinal axis, is exerted on the drive element, which may be either through a direct impact on the drive element by use of the actuating element or a part thereof or, more generally, via one or more additional elements, which may receive an impact from the actuating element or a part thereof and may forward the impact to the drive element.

In a typical embodiment, a sliding element is provided which may be configured to press against an edge of the drive element or against an edge of an element which may be connected to the drive element, in particular, against an edge or a recess of the housing which may partially enclose the drive element or against an edge or a recess of a separate element, which may be inserted between the sliding element and the drive element. The sliding element typically is a part of the actuating element and may be formed as a clamp or pin protruding from the actuating element. By the movement of the actuating element along the actuation path from the initial state to the actuated state, in this particular embodiment, the torque is exerted onto the drive element by application of the sliding element.

When torque is exerted on the drive element in a manner that it sufficiently counteracts the torsional stress exerted by the combined compression and torsion element onto the drive element, the drive element is released from the locking device. The exact moment of a releasing of the drive element from the locking device may depend on an amount of pressure induced on the combined compression and torsion element as well as an extent of a friction of any surface which is involved in this process. Therefore, in a typical embodiment, in order to ease the release of the drive element from the locking device, the housing may be formed that it may comprise a beveled edge which may be particularly configured in a manner to decrease the extent of the friction of the edge of the housing which forms an element of the locking device.

The release of the drive element from the locking device results in a triggering of the lancing motion, typically by providing an impact onto the lancing element as described above. In an optional embodiment, the drive element may comprise a plunger or, alternatively, the drive element may act upon a separate plunger, whereby, in any case, the plunger is adapted to convert the movement of the drive element into the lancing motion by means of an impact of the plunger onto the lancing element. Especially, since the size of the lancing device is reduced with respect to the length of a lancing device known according to the state of the art, wear caused by the impact of the lancing actuator onto the lancing element is considerably increased. It may therefore be advantageous to implement means at least at a side of the plunger which faces the lancing element which are configured to reduce the wear caused by the impact of the plunger onto the lancing element.

In a typical embodiment, at least the side of the plunger which faces the lancing element may comprise a reinforced material. As used herein, the reinforced material exhibits improved mechanical properties with respect to external forces. For the purpose of reducing the wear caused by the impact of the plunger onto the lancing element, a reinforced material which comprises polybutylenterephthalat (PBT), or polyethylenterephthalat (PET), or a blend thereof, polyamide (PA), or polyetheretherketone (PEEK), is of particular benefit.

In another typical embodiment, at least the side of the plunger which faces the lancing element may be armed with or additionally armed with a metallic assembly part, whereby the metallic assembly part may particularly comprise titanium or high-grade steel.

In another embodiment, at least the side of the plunger which faces the lancing element may comprise a part or may additionally comprise a part which is inserted into the plunger in order to increase the mechanical strength of the plunger resulting in an increased wear resistance.

In any of these embodiments, it may be advantageous to shape at least the side of the plunger which faces the lancing element with a contour which, typically tightly, fits into the adjoining surface of the lancing element which is mostly affected by the impact of the plunger. By this kind of typically tight fitting, the wear effects of the plunger on the lancing element are considerably reduced.

In a typical embodiment, prior to a subsequent initial state, the drive element is configured to perform a return motion in order to enable a repeatable use of the lancing device. The return motion of the drive element into the locking device may at least partly, typically only during the last step of the return motion, be exerted by the typically persistent torsional stress of the combined compression and torsion element onto the drive element. Due to the relaxation of the combined compression and torsion element which returns into equilibrium after the lancing motion is completed, no forces or only few tension forces may remain. This, however, means that only a torsional portion of the forces acting upon the combined compression and torsion element persists, which results in a rotation of the combined compression and torsion element about its longitudinal axis in a manner that the drive element is forced to move into the locking device. In order to support the return motion of the drive element into the locking device, a separate return spring may be provided which may be typically designed to counteract the movement of the combined compression and torsion element.

In a particular embodiment, means are provided which are configured to retard the return motion of the drive element. In one aspect thereof, the combined compression and torsion element may be adapted to receive a part of a kinetic energy of the return motion of the drive element as a torsional energy in order to slow down the return motion. In another aspect thereof, the housing may comprise at least one retarding edge and/or at least one retarding recess which may counteract the return motion by a braking effect of the retarding edge and/or recess together with a friction effect of their surfaces.

In an optional embodiment of the present invention, the combined compression and torsion element may be mounted in an advantageous manner between the actuating element and the drive element. Especially, the first end of the combined compression and torsion element may therefore be attached to the actuating element while the second end may be attached to the drive element.

In a specific embodiment, the combined compression and torsion element may be mounted, attached, hooked, or hinged in a manner that it is movable along the longitudinal axis in relation to both the actuating element and the drive element. Hereby, the motion of the combined compression and torsion element may typically but not necessarily be coupled to the motion of the actuating element. In addition, the tensioning movement may typically but not necessarily be coupled to the return movement of the combined compression and torsion element. In order to achieve such couplings, the combined compression and torsion element may be mounted in a manner that the first leg is inserted into a first notch of a first arbor of the actuating element, while the second leg is inserted into a second notch of the second arbor of the drive element. This arrangement may be performed such that the drive element is pivoted against the combined compression and torsion element.

In an alternative configuration, the first end the combined compression and torsion element is firmly connected to the actuating element while the second end is also firmly connected to the drive element. This configuration allows the combined compression and torsion element to receive compression, tension, and torsion at the same time.

In a second aspect of the present invention, a lancing device is disclosed which comprises the lancing actuator as previously described in detail and at least one lancing element adapted for perforating a skin portion of a user during a puncture process. As further used herein, the lancing element is an arbitrary element adapted for perforating a skin portion of a user in order to create one or more openings, punctures or incisions in the skin portion through which the body fluid may be sampled and/or through which the body fluid may leave a body tissue located underneath the skin portion. Thus, generally, the lancing element is a lancet comprising a needle, a blade, or a cannula. The lancet may be a flat lancet, a round lancet or a lancet generally having an arbitrary cross-section, such as a polygonal cross-section.

The lancing element according to the present invention may particularly comprise a lancet body and a lancet tip. Generally, the lancet tip is an arbitrary feature for perforating, also referred to as puncturing, a skin portion of the user. The tip, as an example, may be a round needle tip or an acute needle tip. In addition, the housing typically has an exit opening for the lancet tip in order to perforate a skin portion of the user. Thus, as an example, the housing may comprise an opening leading to a chamber, through which the tip of the lancing element is movable when performing a puncturing motion. As an example, the chamber may have an elongated shape, with a longitudinal axis, wherein the lancing element is stored along the longitudinal axis within the chamber and wherein the lancing element may move along the longitudinal axis, in order for the tip and, optionally, further parts of the lancing element, to leave the chamber in order to perforate the skin portion of the user. The chamber typically may be closed along the walls of the longitudinal axis, and the opening may be at a front face of the chamber. After perforating the skin portion of the user, the lancing element may be retracted into the chamber and may be restored within the chamber. Within the chamber, the lancing element may be stored in a relaxed state. Alternatively, the lancing element may be stored in a bent state, in order to keep the puncture element in place by deformation. Additionally or alternatively, other means for keeping the lancing element in place when stored or restored within the chamber may be present.

In a typical embodiment, the at least one lancing element may comprise a sterile protection which ensures the sterility of the unused lancing elements prior to their use in the puncture process. The sterile protection typically comprises an elastomeric material which is pierced or stripped off by the lancet tip during the puncture process.

Typically, the at least one lancing element may be mechanically coupled to the lancing actuator during the entire puncture process. Hereby, the lancing element may be provided for a single use and may be taken from a magazine which comprises the one or two or more lancing elements which may be successively coupled to a lancet holder. In particular, the magazine may comprise at least a part of the lancing actuator, whereby the magazine may be especially removably coupled to the housing.

In a specific embodiment, an indicating element for indicating an imminent triggering of the puncture process may be provided, wherein the indicating element particularly forms a part of the lancing actuator.

For further details of the lancing device, reference may be made to the disclosure of the lancing actuator, as disclosed above and/or below.

In a further aspect, the medical device may be adapted to perform the following steps, typically in the given order. Still, other orders of the steps are feasible. Further, it is possible to perform two or more of the steps simultaneously or in an overlapping fashion. Further, it is also possible to perform one, two or more of the steps repeatedly. Further, additional steps may be comprised which are not mentioned in the following. The steps are as follows:

a) Triggering an actuating element of the lancing actuator in an initial state by means accessible from the outside of the housing; whereby, in the initial state, a drive element is locked in a locking device under a torsional stress exerted by a combined compression and torsion element;

b) Moving the actuating element along an actuation path from the initial state into an actuated state through the triggering;

c) Exerting a torque on the drive element and tensioning the combined compression and torsion element through the moving of the actuating element;

d) Releasing the drive element from the locking device, typically after a previous unlocking, through the torque which prevails the torsional stress exerted by the combined compression and torsion element;

e) Relaxing the tensioned combined compression and torsion element, wherein the relaxing of the tensioned combined compression and torsion element is performed in full or only partially;

f) Driving the drive element of the lancing actuator through the relaxing of the combined compression and torsion element and guiding it within the housing; and g) Driving a lancing element adapted for sampling a body fluid to perform a lancing motion through the driving of the drive element.

In a typical embodiment, the typically persistent torsional stress of the combined compression and torsion element onto the drive element, prior to a subsequent initial state, may exert a return motion of the drive element into the locking device. Hereby, particularly a separate return spring may support the return motion of the drive element into the locking device. As the return spring, an ordinary spring may be employed, which, particularly in contrast to the combined compression and torsion element, only needs to undergo compression, tension and relaxation but is not subject to receive any torsion.

In a specific embodiment, the return motion of the drive element may be retarded by the combined compression and torsion element, particularly through an embodiment, wherein the combined compression and torsion element may receive a part of a kinetic energy of the return motion of the drive element as a torsional energy, and/or through an alternative embodiment, wherein the housing may comprise at least one retarding edge and/or at least one retarding recess.

In a further typical embodiment, a sliding element, which is particularly shaped as a part of the actuating element, may exert the torque on the drive element, wherein, when the actuating element moves along the actuation path from the initial state into the actuated state, the sliding element typically presses against an edge of the drive element or against an edge of an element which may be connected to the drive element.

In a further typical embodiment, a control track and a control cam may guide the drive element within the housing, wherein the control cam may make a relative movement with respect to the control track during at least a part of a movement of the drive element, wherein, in particular, the control track typically has a guide curve formed by adapted edges and/or recesses of the housing into which the control cam may engage.

For further details of the method, reference may be made to the disclosure of the lancing actuator and/or the lancing device, as disclosed above and/or below.

In a further aspect, a method of generating a sample of a body fluid is disclosed. The method comprises a use of a lancing device by operating a lancing actuator, in particular according to one or more of the embodiments as disclosed above and/or below. The method comprises the following steps, which, typically, may be performed in the given order. However, a different order is possible. It is also possible to perform two of the method steps simultaneously or in an overlapping fashion. Further, it is possible to perform one or two of the method steps repeatedly. The method may comprise additional method steps which are not mentioned in the following. The method steps of the method include:

i) performing a lancing motion by operating the lancing actuator according to any of the embodiments referring to such a method; and ii) driving the lancing element which is adapted for perforating a skin portion of a user during a puncture process, thereby generating the sample of the body fluid.

The following embodiments are typical:

Embodiment 1

A lancing actuator for driving a lancing element for sampling a body fluid, comprising a drive element adapted for driving the lancing element to perform a lancing motion, the drive element being guided within a housing of the lancing actuator, a combined compression and torsion element which, by a relaxing movement of the combined compression and torsion element, is adapted to drive the lancing motion, a combined triggering and driving device having an actuating element and a locking device, wherein the actuating element has an initial state and an actuated state and is accessible from the outside of the housing, wherein, in the initial state, the drive element is locked in the locking device under a torsional stress exerted by the combined compression and torsion element, wherein the combined triggering and driving device is configured in a manner that, when the actuating element makes a movement along an actuation path from the initial state into the actuated state, a torque is exerted on the drive element which prevails the torsional stress exerted by the combined compression and torsion element in a manner that the drive element is released from the locking device, which results in a triggering of the lancing motion.

Embodiment 2

The lancing actuator according to the preceding embodiment, wherein the housing at least partially constitutes an outside enclosure for the lancing actuator.

Embodiment 3

The lancing actuator according to any of the preceding embodiments, wherein the housing at least partially constitutes an interior enclosure for the drive element.

Embodiment 4

The lancing actuator according to any of the preceding embodiments, wherein the relaxing movement of the combined compression and torsion element can be in full or only partially.

Embodiment 5

The lancing actuator according to any of the preceding embodiments, wherein, particularly prior to a subsequent initial state, a return motion of the drive element into the locking device is at least partly, typically only the last step of the return motion, exerted by the typically persistent torsional stress of the combined compression and torsion element onto the drive element.

Embodiment 6

The lancing actuator according to the preceding embodiment, wherein a separate return spring is provided for supporting the return motion of the drive element into the locking device.

Embodiment 7

The lancing actuator according to any of the two preceding embodiments, wherein means are provided which are configured to retard the return motion of the drive element.

Embodiment 8

The lancing actuator according to the preceding embodiment, wherein the combined compression and torsion element is configured to receive a part of a kinetic energy of the return motion of the drive element as a torsional energy.

Embodiment 9

The lancing actuator according to any of the two preceding embodiments, wherein the housing comprises at least a retarding edge and/or at least a retarding recess.

Embodiment 10

The lancing actuator according to any of the preceding embodiments, wherein the drive element comprises a beveled edge which is connected to the locking device, wherein the beveled edge is configured to ease a release of the drive element from the locking device.

Embodiment 11

The lancing actuator according to any of the preceding embodiments, wherein the torque is exerted on the drive element by a sliding element, wherein, when the actuating element makes a movement along the actuation path from the initial state into the actuated state, the sliding element presses against an edge of the drive element or against an edge of an element which is connected to the drive element.

Embodiment 12

The lancing actuator according to the preceding embodiment, wherein the sliding element presses against an edge of the housing which partially encloses the drive element.

Embodiment 13

The lancing actuator according to any of the two preceding embodiments, the sliding element is a part of the actuating element.

Embodiment 14

The lancing actuator according to the preceding embodiment, wherein the sliding element presses against an edge of the drive element.

Embodiment 15

The lancing actuator according to any of the preceding embodiments, wherein the drive element is guided within the housing by means of a control track and a control cam, wherein the control cam makes a relative movement with respect to the control track during at least a part of a movement of the drive element.

Embodiment 16

The lancing actuator according to the preceding embodiment, wherein the control track has a guide curve formed by adapted edges and/or recesses of the housing into which the control cam engages.

Embodiment 17

The lancing actuator according to any of the preceding embodiments, wherein the combined compression and torsion element comprises a longitudinal axis, a first end and a second end, wherein the first end is attached to the actuating element and the second end is attached to the drive element.

Embodiment 18

The lancing actuator according to the preceding embodiment, wherein the first end is configured as a first leg which points vertically in relation to the longitudinal axis, wherein the second end is configured as a second leg which points vertically in relation to the longitudinal axis, and wherein the combined compression and torsion element executes a torque about the longitudinal axis by a twisting motion of the first leg relative to the second leg.

Embodiment 19

The lancing actuator according to the two preceding embodiments, wherein the combined compression and torsion element is mounted in a manner that it is movable along the longitudinal axis in relation to the actuating element and in relation to the drive element.

Embodiment 20

The lancing actuator according to the preceding embodiment, wherein the motion of the combined compression and torsion element is coupled to the motion of the actuating element.

Embodiment 21

The lancing actuator according to the two preceding embodiments, wherein the tensioning movement is coupled to the return movement of the combined compression and torsion element.

Embodiment 22

The lancing actuator according to the three preceding embodiments, wherein the combined compression and torsion element is mounted in a manner that the first leg is inserted into a first notch of a first arbor of the actuating element and/or the second leg is inserted into a second notch of the second arbor of the drive element.

Embodiment 23

The lancing actuator according to the preceding embodiment, wherein the drive element is pivoted against the combined compression and torsion element.

Embodiment 24

The lancing actuator according to any of the embodiments 17 or 18, wherein the first end is firmly connected to the actuating element and the second end is firmly connected to the drive element.

Embodiment 25

The lancing actuator according to any of the preceding embodiments, wherein the combined compression and torsion element comprises at least one helical spring.

Embodiment 26

The lancing actuator according to any of the preceding embodiments, wherein the actuating element comprises an operating button which is mounted in a manner that it faces away from the lancing element.

Embodiment 27

The lancing actuator according to the preceding embodiment, wherein the operating button is mounted at a rear end of the housing.

Embodiment 28

The lancing actuator according to any of the preceding embodiments, wherein a stop is provided which is adapted to halt a forward movement of the drive element, by which the lancing motion is reversed.

Embodiment 29

The lancing actuator according to any of the preceding embodiments, wherein the stop forms a part of the housing.

Embodiment 30

The lancing actuator according to any of the preceding embodiments, wherein the drive element comprises a plunger which is adapted to convert the movement of the drive element into the lancing motion by means of an impact of the plunger onto the lancing element.

Embodiment 31

The lancing actuator according to the preceding embodiment, wherein means are implemented at least at a side of the plunger which faces the lancing element, wherein the means are configured to reduce a wear which is caused by the impact of the plunger onto the lancing element.

Embodiment 32

The lancing actuator according to the preceding embodiment, wherein at least the side of the plunger which faces the lancing element comprises a reinforced material.

Embodiment 33

The lancing actuator according to the preceding embodiment, wherein the reinforced material comprises polybutylenterephthalat (PBT), or polyethylenterephthalat (PET), or a blend thereof, polyamide (PA), or polyetheretherketone (PEEK).

Embodiment 34

The lancing actuator according to any of the three preceding embodiments, wherein at least the side of the plunger which faces the lancing element is armed with a metallic assembly part.

Embodiment 35

The lancing actuator according to the preceding embodiment, wherein the metallic assembly part comprises titanium or high-grade steel.

Embodiment 36

The lancing actuator according to any of the five preceding embodiments, wherein at least the side of the plunger which faces the lancing element comprises an inserted part.

Embodiment 37

The lancing actuator according to any of the six preceding embodiments, wherein at least the side of the plunger which faces the lancing element is fitted with a contour which, typically tightly, fits into the adjoining surface of the lancing element.

Embodiment 38

A lancing device, comprising the lancing actuator according to any of the preceding embodiments, the lancing device further comprising at least one lancing element adapted for perforating a skin portion of a user during a puncture process.

Embodiment 39

The lancing device according to the preceding embodiment, wherein the at least one lancing element is mechanically coupled to the lancing actuator during the entire puncture process.

Embodiment 40

The lancing device to any of the two preceding embodiments, wherein the at least one lancing element has a lancet body and a lancet tip.

Embodiment 41

The lancing device according to the preceding embodiment, wherein the housing has an exit opening for the lancet tip.

Embodiment 42

The lancing device according to the preceding embodiment, wherein a magazine 164 is provided which comprises the at least one lancing element 166 which can be successively coupled to a lancet holder.

Embodiment 43

The lancing device according to the preceding embodiment, wherein the magazine comprises at least a part of the lancing actuator.

Embodiment 44

The lancing device according to any of the two preceding embodiments, wherein the magazine is removably coupled to the housing.

Embodiment 45

The lancing device according to any of the preceding embodiments referring to a lancing device, wherein the at least one lancing element comprises a sterile protection which ensures the sterility of the unused lancing elements prior to their use in the puncture process.

Embodiment 46

The lancing device according to the preceding embodiment, wherein the sterile protection comprises an elastomeric material which is pierced or stripped off by the lancet tip during the puncture process.

Embodiment 47

The lancing device according to any of the preceding embodiments referring to a lancing device, wherein an indicating element for indicating an imminent triggering of the puncture process is provided.

Embodiment 48

The lancing device according to the preceding embodiment, wherein the indicating element forms a part of the lancing actuator.

Embodiment 49

A method for performing a lancing motion by operating the lancing actuator according to any of the preceding embodiments referring to a lancing actuator, the method comprising the following steps:
  a) Triggering an actuating element of the lancing actuator in an initial state by means accessible from the outside of the housing; whereby, in the initial state, a drive element is locked in a locking device under a torsional stress exerted by a combined compression and torsion element;
  b) Moving the actuating element along an actuation path from the initial state into an actuated state through the triggering;
  c) Exerting a torque on the drive element and tensioning the combined compression and torsion element through the moving of the actuating element;
  d) Releasing the drive element from the locking device through the torque which prevails the torsional stress exerted by the combined compression and torsion element;
  e) Relaxing the tensioned combined compression and torsion element;
  f) Driving the drive element of the lancing actuator through the relaxing of the combined compression and torsion element and guiding it within the housing; and
  g) Driving a lancing element adapted for sampling a body fluid to perform a lancing motion through the driving of the drive element.

Embodiment 50

The method according to the preceding embodiment, wherein the relaxing of the tensioned combined compression and torsion element is performed in full or only partially.

Embodiment 51

The method according to any of the two preceding embodiments, wherein, particularly prior to a subsequent initial state, the typically persistent torsional stress of the combined compression and torsion element onto the drive element exerts a return motion of the drive element into the locking device.

Embodiment 52

The method according to the preceding embodiment, wherein a separate return spring supports the return motion of the drive element into the locking device.

Embodiment 53

The method according to any of the two preceding embodiments, wherein the return motion of the drive element is retarded by the combined compression and torsion element.

Embodiment 54

The method according to the preceding embodiment, wherein the combined compression and torsion element receives a part of a kinetic energy of the return motion of the drive element as a torsional energy.

Embodiment 55

The method according to any of the four preceding embodiments, wherein the return motion of the drive element is retarded by the housing which comprises at least one retarding edge and/or at least one retarding recess.

Embodiment 56

The method according to any preceding embodiments referring to a method, wherein a sliding element exerts the torque on the drive element, wherein, when the actuating element moves along the actuation path from the initial state into the actuated state, the sliding element presses against an edge of the drive element or against an edge of an element which is connected to the drive element.

Embodiment 57

The method according to the preceding embodiment, wherein the sliding element is a part of the actuating element and typically presses against an edge of the drive element.

Embodiment 58

The method according to any preceding embodiments referring to a method, wherein a control track and a control cam guide the drive element within the housing, wherein the control cam makes a relative movement with respect to the control track during at least a part of a movement of the drive element.

Embodiment 59

The method according to the preceding embodiment, wherein the control track typically has a guide curve formed by adapted edges and/or recesses of the housing into which the control cam engages.

Embodiment 60

A method of generating a sample of a body fluid, the method comprising a use of the lancing device, according to any of the preceding embodiments referring to a lancing device, the method comprising
i) Performing a lancing motion by operating the lancing actuator according to any of the preceding embodiments referring to such a method;
ii) Driving the lancing element which is adapted for perforating a skin portion of a user during a puncture process, thereby generating the sample of the body fluid.

BRIEF DESCRIPTION OF THE DRAWINGS

Further optional features and embodiments will be disclosed in more detail in the subsequent description of typical embodiments, typically in conjunction with the dependent claims. Therein, the respective optional features may be realized in an isolated fashion as well as in any arbitrary feasible combination, as the skilled person will realize. The scope of the invention is not to be restricted to the disclosed embodiments. The embodiments are schematically depicted in the Drawings. Therein, identical reference numbers in these Drawings refer to identical or functionally comparable elements.

In the Drawings,

FIG. 1 shows a perspective view of a first embodiment of a lancing actuator which is partially enclosed within a housing;

FIG. 2 displays a perspective view (FIG. 2A), a side view (FIG. 2B), and an aerial view (FIG. 2C), each of the first embodiment of the lancing actuator, wherein the housing is only partially displayed, and wherein, in the initial state, the drive element is locked in the locking device under a torsional stress exerted by the combined compression and torsion element;

FIG. 3 exhibits a perspective view (FIG. 3A), a side view (FIG. 3B), and an aerial view (FIG. 3C), each of the first embodiment of the lancing actuator, wherein an actuating element makes a movement along an actuation path from the initial state into the actuated state, while still no torque is exerted;

FIG. 4 shows a perspective view (FIG. 4A), a side view (FIG. 4B), and an aerial view (FIG. 4C), each of the first embodiment of the lancing actuator, wherein a torque is exerted on the drive element which counteracts the torsional stress exerted by the combined compression and torsion element;

FIG. 7 shows a perspective view of the first embodiment of the lancing actuator, wherein the torsional stress of the combined compression and torsion element onto the drive element exerts a return motion of the drive element into the locking device, supported here by a separate return spring;

FIG. 8 displays a perspective view (FIG. 8A), a side view (FIG. 8B), and an aerial view (FIG. 8C), each of the first embodiment of the lancing actuator, wherein the drive element is again locked in the locking device.

FIG. 9 shows a perspective view of a second embodiment of a lancing actuator (FIG. 9A) which is partially enclosed with a housing (FIG. 9B);

FIG. 10 displays shows a further perspective view of the second embodiment of a lancing actuator, wherein a torque which is exerted on the drive element counteracts the torsional stress of the combined compression and torsion element, by which the drive element will soon be released from the locking device, resulting in a triggering of the lancing motion;

FIG. 11 exhibits a further perspective view of the second embodiment of the lancing actuator, wherein the lancing actuator drives the lancing element to perforate a skin portion of a user during a puncture process;

DETAILED DESCRIPTION OF THE EMBODIMENTS

Figure 5:
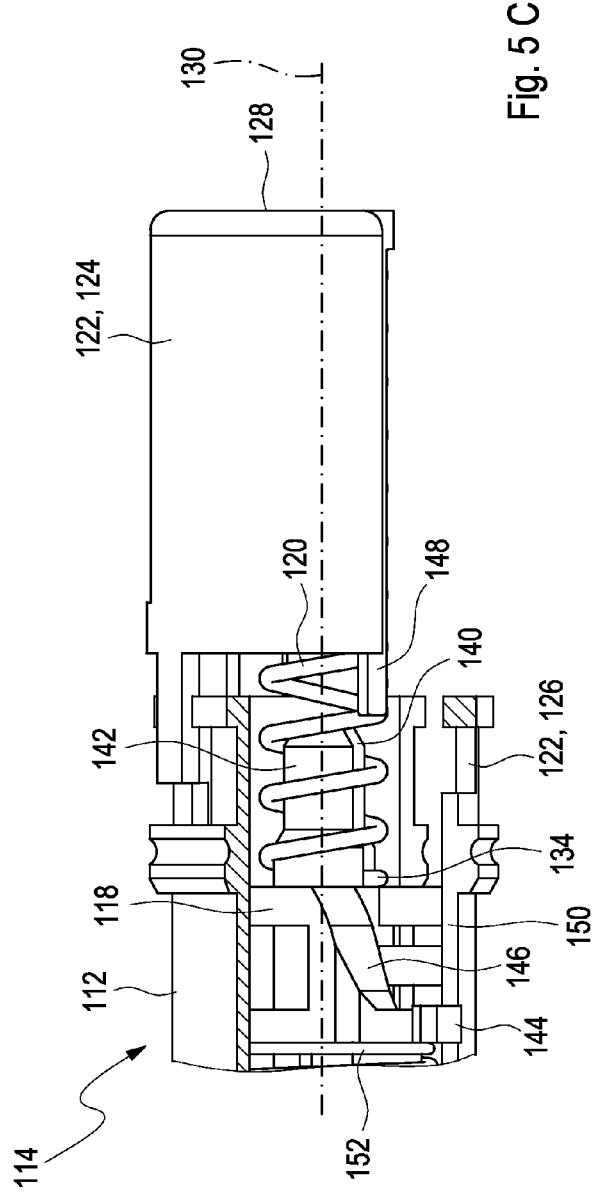
FIG. 5 displays a perspective view (FIG. 5A), a side view (FIG. 5B), and an aerial view (FIG. 5C), each of the first embodiment of the lancing actuator, wherein the torque which is exerted on the drive element counteracts the torsional stress of the combined compression and torsion element, by which the drive element is released from the locking device, resulting in a triggering of the lancing motion.

FIG. 1 shows, partially enclosed within a housing 112 which is, for illustration purposes only, predominantly removed in FIG. 2A, a perspective view of a first embodiment of a lancing actuator 114. The lancing actuator 114 is a part of a lancing device which further comprises a lancing element (not depicted here) which is adapted for perforating a skin portion of a user during a puncture process. Here, the lancing element is mechanically coupled to the lancing actuator 114 during the entire puncture process.

The lancing actuator 114 is configured for driving the lancing element for sampling a body fluid and, therefore, comprises a drive element 118 adapted for driving the lancing element to perform a lancing motion. The drive element 118 is guided within the housing 112 which partially also encloses the lancing actuator 114.

The lancing actuator 114 further comprises a combined compression and torsion element 120 which is adapted to drive the lancing motion of the lancing element by a relaxing movement of the combined compression and torsion element 120. The lancing actuator 114 further comprises a combined triggering and driving device 122 which includes an actuating element 124 and a locking device 126. The actuating element 124 is accessible from the outside of the housing through an operating button 128 which is mounted at a rear end of the actuating element 124 in a manner that it faces away from the lancing element.

FIGS. 1 and 2A-C display an initial state of the actuating element 124, wherein the drive element 118 is locked in the locking device 126 under a torsional stress which is exerted by the combined compression and torsion element 120 being twisted in a respective manner. In particular, FIG. 2B discloses that the combined compression and torsion element 120 is accomplished as a helical spring which comprises a longitudinal axis 130, a first end 132 and a second end 134. Hereby, the first end 132 is configured as a first leg which points vertically in relation to the longitudinal axis 130 and is attached to the actuating element 124 by flexibly inserting the first leg 132 into a first notch 136 of a first arbor 138 of the actuating element 124, whereas the second end 134 is configured as a second leg which points vertically in relation to the longitudinal axis 130 and is attached to the drive element 118 by flexibly inserting the second leg 134 into a second notch 140 of a second arbor 142 of the drive element 118.

Consequently, the combined compression and torsion element 120 is mounted in a manner that it is movable along the longitudinal axis 130 in relation to the actuating element 124 and in relation to the drive element 118, while, at the same time the combined compression and torsion element 120 is twistable about the longitudinal axis 130 by a relative motion of the first leg 132 with relation to the second leg 134. This arrangement accomplishes that the motion of the combined compression and torsion element 120 is coupled to the motion of the actuating element 124. In particular, FIG. 2C discloses that the drive element 118 comprises a protruding edge 144 which firmly locks the drive element 118 during the initial state of the actuating element 124 into the locking device 126. In addition, the drive element 118 comprises a beveled edge 146, wherein the beveled edge 146 is configured in a manner to ease a release of the drive element 118 from the locking device 126 as will be described later.

FIGS. 3A-C show the situation after a triggering of the actuating element 124 has been affected by means of the operating button 128 which is mounted at the rear end of the actuating element 124 and which is accessible from the outside. The triggering effects a movement of the actuating element 124 along an actuation path from the initial state into an actuated state, which is constantly compressing the combined compression and torsion element 120 to accomplish a tension within the combined compression and torsion element 120. Here, the actuating element 124 comprises a sliding element 148, which is a fixed part of the actuating element 124 and which, therefore, moves together with the actuating element 124 along the actuation path directed towards the beveled edge 146 of the drive element 118.

In particular, FIG. 3C discloses that the sliding element 148 is attached at the actuating element 124 in a manner that will be able to slide along the beveled edge 146 after it has reached the drive element 118. While previously no torque has been exerted on the combined compression and torsion element 120, by this kind of movement of the sliding element 148 along the beveled edge 146, the drive element 118 now increasingly turns along its longitudinal axis 130. Since the second leg 134 of the combined compression and torsion element 120 is, as described above, attached to the drive element 118 through the second notch 140 of the second arbor 142, the combined compression and torsion element 120 receives an increasing torque.

FIGS. 4A-C show the moment when the sliding element 148 has just reached the beveled edge 146 of the drive element 118 at a point where it is able to unlock the protruding edge 144 from the part of the locking device 126 forming a part of the drive element 118. In this moment, the torque which is exerted on the drive element 118, prevails the torsional stress exerted by the combined compression and torsion element 120. In addition, until now the movement of the actuating element 124 has been constantly compressing the combined compression and torsion element 120 to accomplish a tension within the combined compression and torsion element 120.

FIGS. 5A-C display the situation after the protruding edge 144 forming a part of the drive element 118 has been released from the locking device 126 which results in a sudden accelerating movement of the drive element 118, whereby the protruding edge 144 of the drive element 118 acts as a control cam which is guided along a control track 150. The control track 150 exhibits a guide curve which is formed by specifically adapted edges and/or recesses of the housing into which the protruding edge 144 engages as control cam. This movement of the drive element 118 starts to compress a return spring 152, which had not been involved in the actuating process so far. As depicted in FIG. 5A, by moving towards an exit opening 154 in the housing 112, the movement of the drive element 118 at the same time commences to trigger the lancing motion of the lancing element which will soon allow a lancet tip to exit the lancing device.

As shown in FIG. 5A, the drive element 118 here comprises a part which acts as a plunger 156 being adapted to convert the movement of the drive element 118 into the lancing motion by means of an impact of the plunger 156 onto the lancing element. In order to reduce a wear which is caused by the impact of the plunger 156 onto the lancing element, respective means are implemented at a side of the plunger 156 which faces the lancing element. Therefore, the side of the plunger 156 which faces the lancing element comprises a reinforced material, which particularly comprises polybutylenterephthalat (PBT), or polyethylenterephthalat (PET), or a blend thereof, polyamide (PA), or polyetheretherketone (PEEK), or is armed with a metallic assembly part, which typically comprises titanium or high-grade steel. In addition, the side of the plunger 156 which faces the lancing element is fitted with a contour which tightly fits into the adjoining surface of the lancing element.

Figure 6:
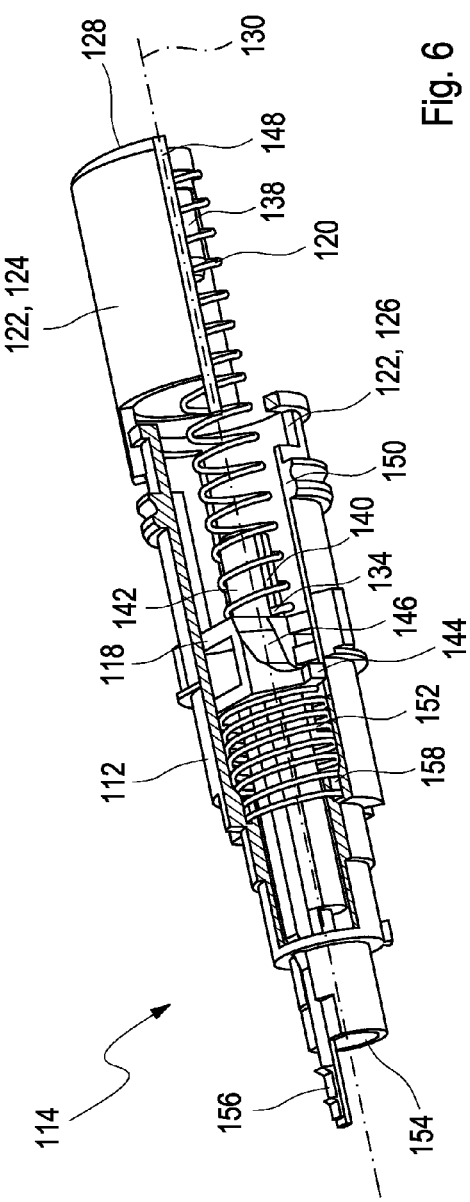
FIG. 6 exhibits a perspective view of the first embodiment of the lancing actuator, wherein the lancing actuator drives the lancing element to perforate a skin portion of a user during a puncture process.

FIG. 6 exhibits the moment at which the lancing actuator 114 has driven the lancing element to a position furthest from the exit opening 154 in the housing 112. At this moment, the lancet tip, when applied to a puncture process, has already perforated a skin portion of a user. At the same time, the drive element 118 is stopped by a stop (abutment) 158 which is formed by a part of the housing and which is adapted to halt the forward movement of the drive element 118, and the return spring 152 also shows maximal tension.

FIG. 7 discloses the situation wherein the persistent torsional stress of the combined compression and torsion element 120 onto the drive element 118 exerts a return motion of the drive element 118 into the locking device 126 along the control track 150. In this embodiment, the movement of the drive element 118 returning into the locking device 126 is supported by a relaxation of the separate return spring 152. Along the control track 150, means (not depicted here) in form of retarding edges and retarding recesses along the housing are provided in order to retard the return motion of the drive element 118. In addition, the control track may be designed such that a part of the kinetic energy is transferred into torsional energy. For example, this may be realized via an ascending part within the rear part of the control track.

FIG. 8A-C display the moment at which the drive element 118, like shown in FIGS. 1 and 2 A-C, is again locked in the locking device 126 by means of the protruding edge 144, supported by the remaining torsional stress of the combined compression and torsion element 120. The drive element 118 is now waiting until a further triggering of the lancing device repeats the actuating and puncturing process as described herein.

FIG. 9A-B show a perspective view of a second embodiment of the lancing actuator 114, partially enclosed with the housing 112 which is, for illustration purposes only, predominantly removed in FIG. 9A. The lancing actuator 114 is a part of the lancing device which further comprises the lancing element adapted for perforating the skin portion of the user during the puncture process. The lancing actuator 114 which is configured to drive the lancing element for sampling a body fluid, comprises the drive element 118 adapted for driving the lancing element to perform the lancing motion. The drive element 118 is guided within the housing 112 which partially also encloses the lancing actuator 114. The lancing actuator 114 further comprises the combined compression and torsion element 120 adapted to drive the lancing motion of the lancing element by the relaxing movement of the combined compression and torsion element 120. The lancing actuator 114 further comprises the combined triggering and driving device 122 which includes the actuating element 124 and the locking device 126, whereby the actuating element 124 is accessible from the outside of the housing through the operating button 128.

FIG. 9 displays the initial state of the actuating element 124, wherein the drive element 118 is locked in the locking device 126 under a torsional stress exerted by the combined compression and torsion element 120 being twisted in a respective manner. The combined compression and torsion element 120 is accomplished as a helical spring which comprises the longitudinal axis 130, the first end 132 and the second end 134, and is mounted in a manner that the first end 132 is fixed to the actuating element 124, while the second end 134 is fixed to the drive element 118. By this kind of mounting, the combined compression and torsion element 120 is able to receive compression, tension, and torsion. In particular, FIG. 9B discloses that the drive element 118 comprises a protruding edge 144 firmly locking the protruding edge 144 of the drive element 118 during the initial state of the actuating element 124 into the locking device 126. This locking is supported by the combined compression and torsion element 120 which is kept here under a tensional stress, in particular by means of a return spring (not shown here).

In contrast to the first embodiment as displayed in FIGS. 1-8, in the second embodiment as shown in FIGS. 9-12 the torsion points into the opposite direction. Consequently, the second embodiment comprises a control track 150 which is arranged, with respect to the longitudinal axis 130, on the other side of the housing 112 compared with the first embodiment.

FIG. 10 shows the situation after the triggering of the actuating element 124 has been affected by the operating button 128. The movement of the actuating element 124 along the actuation path from the initial state into the actuated state constantly compresses the combined compression and torsion element 120 to accomplish a tension within. As displayed in FIG. 10, the sliding element 148 being part of the actuating device 124 is about to unlock the protruding edge 144 from the part of the housing 112 forming the locking device 126. The torque exerted on the drive element 118 will soon prevail the torsional stress exerted by the combined compression and torsion element 120 and release the protruding edge 144 from the locking device 126.

FIG. 11 exhibits the moment at which the lancing actuator 114 has driven the lancing element to the position furthest from the exit opening 154 in the housing 112 by means of an overshooting of the combined compression and torsion element 120. At the same moment, the drive element 118 is stopped by a stop (abutment) 160 which is formed by a part of the drive element 118, and the relaxation of the separate return spring (not depicted here) supports the return motion of the drive element 118 into the locking device 126.

Figure 12:
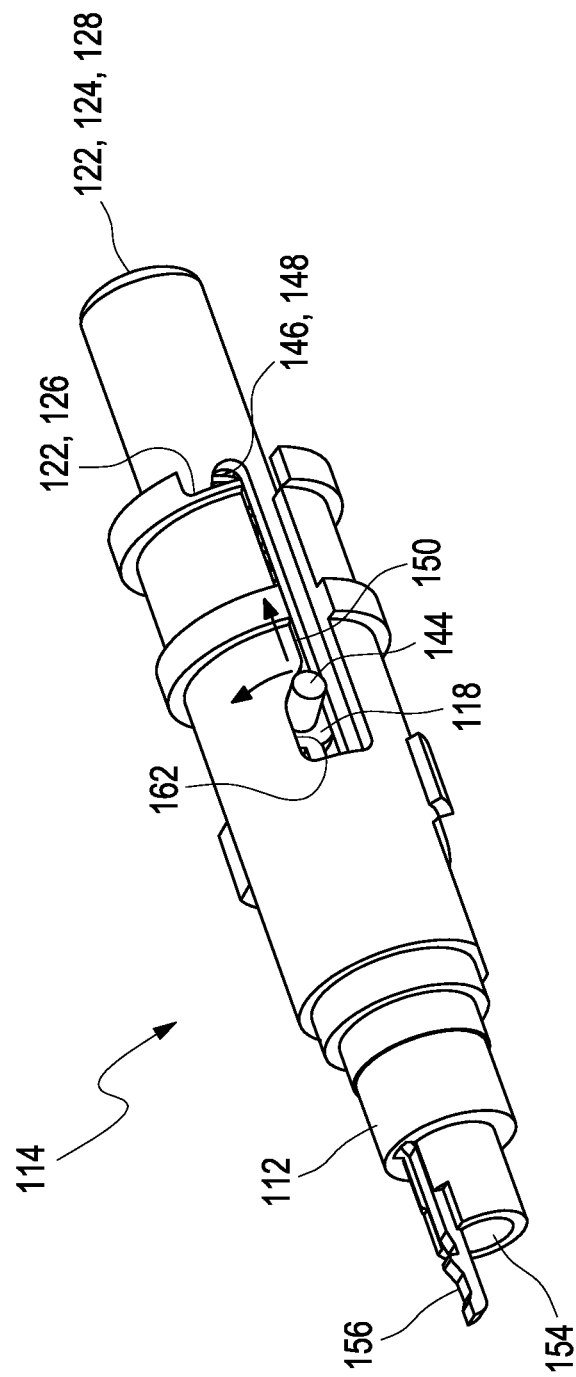
FIG. 12 shows a further perspective view of the second embodiment of the lancing actuator, wherein the torsional stress of the combined compression and torsion element onto the drive element exerts a return motion of the drive element into the locking device which is, however, retarded by a retarding edge of the housing.
Figure 13:
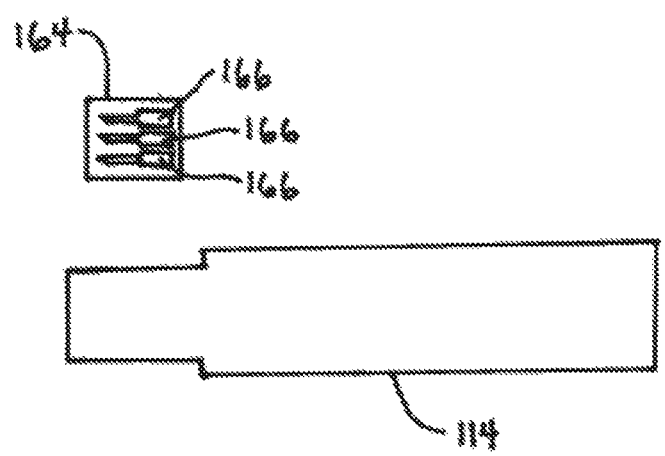
FIG. 13 is a schematic view of a lancing actuator and a magazine.

FIG. 12 displays the situation during the return motion of the drive element 118 during which the drive element 118 is retarded along the control track 150 by the protruding edge 144 meeting a retarding recess 162 which forms a part of the housing 112. The protruding edge 144 is released from the retarding recess 162 by the separate compression spring (not depicted here) which drives the protruding edge 144 further along the control track 150 back to the locking device 126. By this movement of the protruding edge 144, the drive element 118 is turned in a manner that the combined compression and torsion element 120 which is firmly mounted with the drive element 118 receives a torsional stress by which torque the drive element 118 will be locked within the locking device 126 via the protruding edge 144 prior to a further triggering.

LIST OF REFERENCE NUMBERS 112 housing
114 lancing actuator
118 drive element
120 combined compression and torsion element
122 combined triggering and driving device 124 actuating element
126 locking device
128 operating button
130 longitudinal axis of the combined compression and torsion element
132 first end (first leg) of the combined compression and torsion element
134 second end (second leg) of the combined compression and torsion element
136 first notch of the first arbor of the actuating element
138 first arbor of the actuating element
140 second notch of the second arbor of the driving element
142 second arbor of the driving element
144 protruding edge of the drive element; control cam
146 beveled edge of the drive element
148 sliding element
150 control track
152 return spring
154 exit opening in the housing
156 plunger
158 stop (abutment) being a part of the housing
160 stop (abutment) being a part of the drive element
162 retarding recess
164 magazine
166 lancing element

The invention claimed is:

1. A lancing actuator for driving a lancing element for sampling a body fluid, comprising:
a drive element adapted for driving the lancing element to perform a lancing motion, the drive element being guided within a housing of the lancing actuator,
a combined compression and torsion element which, by a relaxing movement of the combined compression and torsion element, is adapted to drive the lancing motion, and
a combined triggering and driving device having an actuating element and a locking device, wherein the actuating element has an initial state and an actuated state and is accessible from the outside of the housing, wherein, in the initial state, the drive element is locked in the locking device under a torsional stress exerted by the combined compression and torsion element, wherein the combined triggering and driving device is configured in a manner that, when the actuating element completes a movement along an actuation path from the initial state into the actuated state, a torque is exerted on the drive element which opposes and exceeds the torsional stress exerted by the combined compression and torsion element in a manner that the drive element is released from the locking device, which results in a triggering of the lancing motion.

2. The lancing actuator of claim 1, wherein a return motion of the drive element into the locking device is at least partly effected by the torsional stress of the combined compression and torsion element onto the drive element.

3. The lancing actuator of claim 2, further comprising means configured to retard the return motion of the drive element.

4. The lancing actuator of claim 1, wherein the housing comprises a beveled edge which is connected to the locking device, wherein the beveled edge is configured to ease a release of the drive element from the locking device.

5. The lancing actuator of claim 1, wherein the torque is exerted on the drive element by a sliding element, wherein, when the actuating element makes a movement along the actuation path from the initial state into the actuated state, the sliding element presses against an edge of the drive element or against an edge of an element which is connected to the drive element.

6. The lancing actuator of claim 1, wherein the combined compression and torsion element comprises a longitudinal axis, a first end and a second end, wherein the first end is attached to the actuating element and the second end is attached to the drive element.

7. The lancing actuator of claim 6, wherein the first end is configured as a first kg which points vertically in relation to the longitudinal axis, wherein the second end is configured as a second leg which points vertically in relation to the longitudinal axis, and wherein the combined compression and torsion element is twistable about the longitudinal axis by a relative motion of the first leg with relation to the second leg.

8. The lancing actuator of claim 7, wherein the combined compression and torsion element is mounted in a manner that it is movable along the longitudinal axis in relation to the actuating element and in relation to the drive element.

9. The lancing actuator of claim 6, wherein the combined compression and torsion element is mounted in a manner that it is movable along the longitudinal axis in relation to the actuating element and in relation to the drive element.

10. The lancing actuator of claim 1, wherein the drive element comprises a plunger which is adapted to convert the movement of the drive element into the lancing motion by an impact of the plunger onto the lancing element.

11. The lancing actuator of claim 10, wherein means are implemented at least at a side of the plunger which faces the lancing element, wherein the means are configured to reduce a wear which is caused by the impact of the plunger onto the lancing element.

12. The lancing actuator of claim 11, wherein at least the side of the plunger which faces the lancing element comprises a reinforced material.

13. The lancing actuator of claim 12, wherein at least the side of the plunger which faces the lancing element is armed with a metallic assembly part.

14. The lancing actuator of claim 11, wherein at least the side of the plunger which faces the lancing element is armed with a metallic assembly part.

15. A lancing device, comprising the lancing actuator of claim 1, the lancing device further comprising at least one lancing element adapted for perforating a skin portion of a user during a puncture process wherein the at least one lancing element is mechanically coupled to the lancing actuator during the entire puncture process.

16. The lancing device of claim 15, wherein a magazine is provided which comprises the at least one lancing element which can be successively coupled to a lancet holder.

17. A lancing actuator for driving a lancing element for sampling a body fluid, comprising:
a drive element adapted for driving the lancing element to perform a lancing motion, the drive element being guided within a housing of the lancing actuator,
a combined compression and torsion element which, by a relaxing movement of the combined compression and torsion element, is adapted to drive the lancing motion along a longitudinal axis,
a combined triggering and driving device having an actuating element and a locking device, wherein the actuating element has an initial state and an actuated state and is accessible from the outside of the housing, wherein, in the initial state, the drive element is locked in the locking device under a torsional stress exerted by the combined compression and torsion element, wherein the combined triggering and driving device includes a longitudinally extending sliding element that, when the actuating element completes a movement along an actuation path from the initial state into the actuated state, engages a beveled edge coupled with the drive element to thereby exert a torque on the drive element as the sliding element is longitudinally and slidingly advanced relative to the beveled edge and wherein, when an opposing torque exerted on the drive element by the longitudinal advancement of the sliding element exceeds the torsional stress exerted by the combined compression and torsion element, the drive element is released from the locking device which results in a triggering of the lancing motion.

18. The lancing actuator of claim 17, wherein the beveled edge is disposed on the housing and is connected to the locking device, wherein the beveled edge is configured to ease a release of the drive element from the locking device.

19. The lancing actuator of claim 17, wherein the beveled edge is disposed on the drive element or an element which is connected to the drive element, wherein, when the actuating element makes a movement along the actuation path from the initial state into the actuated state, the sliding element presses against an edge of the drive element or against an edge of the element which is connected to the drive element which forms the beveled edge.

20. A method for performing a lancing motion by operating a lancing actuator, comprising:
   a) triggering an actuating element of a lancing actuator in an initial state by means accessible from the outside of a housing; whereby, in an initial state, a drive element is locked in a locking device under a torsional stress exerted by a combined compression and torsion element;
   b) moving the actuating element along an actuation path from the initial state into an actuated state through the triggering;
   c) exerting a torque on the drive element and tensioning the combined compression and torsion element through the moving of the actuating element;
   d) releasing the drive element from the locking device through the torque which opposes and exceeds the torsional stress exerted by the combined compression and torsion element;
   e) relaxing the tensioned combined compression and torsion element;
   f) driving the drive element of the lancing actuator through the relaxing of the combined compression and torsion element and guiding it within the housing; and
   g) driving a lancing element adapted for sampling a body fluid to perform a lancing motion through the driving of the drive element.

21. The method of claim 20, wherein the torsional stress of the combined compression and torsion element onto the drive element effects a return motion of the drive element into the locking device.

22. The method of claim 21, wherein a sliding element exerts the torque on the drive element, wherein, when the actuating element moves along the actuation path from the initial state into the actuated state, the sliding element presses against an edge of the drive element or against an edge of an element which is connected to the drive element.

23. The method of claim 20, wherein a sliding element exerts the torque on the drive element, wherein, when the actuating element moves along the actuation path from the initial state into the actuated state, the sliding element presses against an edge of the drive element or against an edge of an element which is connected to the drive element.

24. A method for performing a lancing motion by operating a lancing actuator, comprising:
   a) triggering an actuating element of a lancing actuator in an initial state by means accessible from the outside of a housing; whereby, in an initial state, a drive element is locked in a locking device under a torsional stress exerted by a combined compression and torsion element, the combined compression and torsion element having first and second ends wherein the first end is rotationally secured to relative to the actuating element and second end is rotationally secured relative to the drive element to thereby transmit torsional forces between the actuating element and the drive element;
   b) moving the actuating element along an actuation path from the initial state into an actuated state through the triggering;
   c) exerting a torque on the drive element and tensioning the combined compression and torsion element through the moving of the actuating element;
   d) releasing the drive element from the locking device through the torque which opposes and exceeds the torsional stress exerted by the combined compression and torsion element;
   e) relaxing the tensioned combined compression and torsion element;
   f) driving the drive element of the lancing actuator through the relaxing of the combined compression and torsion element and guiding it within the housing; and
   g) driving a lancing element adapted for sampling a body fluid to perform a lancing motion through the driving of the drive element.

25. The method of claim 24, wherein a longitudinally extending sliding element exerts the torque on the drive element, wherein, when the actuating element moves along the actuation path from the initial state into the actuated state, the sliding element is longitudinally advanced and presses against an edge of the drive element or against an edge of an element which is connected to the drive element to thereby exert the torque on the drive element.

26. The method of claim 25, wherein a longitudinally extending sliding element exerts the torque on the drive element, wherein, when the actuating element moves along the actuation path from the initial state into the actuated state, the sliding element is longitudinally advanced and presses against an edge of the drive element or against an edge of an element which is connected to the drive element to thereby exert the torque on the drive element.

* * * * *